United States Patent
Saito et al.

(10) Patent No.: US 11,335,861 B2
(45) Date of Patent: May 17, 2022

(54) ORGANIC PHOTOELECTRIC CONVERSION ELEMENT

(71) Applicants: SONY CORPORATION, Tokyo (JP); SONY SEMICONDUCTOR SOLUTIONS CORPORATION, Kanagawa (JP)

(72) Inventors: Yosuke Saito, Tokyo (JP); Ichiro Takemura, Kanagawa (JP); Osamu Enoki, Kanagawa (JP); Yuki Negishi, Kanagawa (JP); Yuta Hasegawa, Kanagawa (JP); Hideaki Mogi, Kanagawa (JP); Yasuharu Ujiie, Kanagawa (JP)

(73) Assignee: Sony Corporation, Tokyo (JP)

( * ) Notice: Subject to any disclaimer, the term of this patent is extended or adjusted under 35 U.S.C. 154(b) by 41 days.

(21) Appl. No.: 16/612,139

(22) PCT Filed: May 7, 2018

(86) PCT No.: PCT/JP2018/017595
§ 371 (c)(1),
(2) Date: Nov. 8, 2019

(87) PCT Pub. No.: WO2018/207722
PCT Pub. Date: Nov. 15, 2018

(65) Prior Publication Data
US 2020/0168815 A1 May 28, 2020

(30) Foreign Application Priority Data

May 8, 2017 (JP) .............................. JP2017-092150
Feb. 13, 2018 (WO) .................. PCT/JP2018/004854

(51) Int. Cl.
*H01L 51/00* (2006.01)
*C07D 495/04* (2006.01)
(Continued)

(52) U.S. Cl.
CPC ........ *H01L 51/0074* (2013.01); *C07D 495/04* (2013.01); *H01L 51/0046* (2013.01);
(Continued)

(58) Field of Classification Search
CPC .................................................. H01L 51/0074
See application file for complete search history.

(56) References Cited

U.S. PATENT DOCUMENTS 5,358,660 A 10/1994 Kidoh et al.
10,608,049 B2 * 3/2020 Murata .............. H04N 9/04563
(Continued)

FOREIGN PATENT DOCUMENTS

JP 2002-076391 A 3/2002
JP 2009-267134 A 11/2009
(Continued)

OTHER PUBLICATIONS

International Search Report and Written Opinion issued in connection with PCT Application No. PCT/JP2018/017595, dated Jul. 24, 2018. (24 pages).

*Primary Examiner* — William D Young
(74) *Attorney, Agent, or Firm* — K&L Gates LLP

(57) ABSTRACT

A photoelectric conversion element uses organic materials and is provided with improved quantum efficiency and response rate. The organic photoelectric conversion element includes, in a photoelectric conversion layer, p-type molecules represented by Formula (1):

[Chem. 1]

Formula (1)

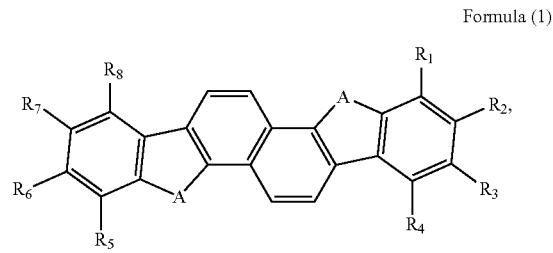

in which A represents any one of oxygen, sulfur or selenium, any one of $R_1$ to $R_4$ represents a substituted or unsubstituted
(Continued)

aryl or heteroaryl having 4 to 30 carbon atoms, the remainder of $R_1$ to $R_4$ each represent hydrogen, any one of $R_5$ to $R_8$ represents a substituted or unsubstituted aryl or heteroaryl having 4 to 30 carbon atoms, and the remainder of $R_5$ to $R_8$ each represent hydrogen.

15 Claims, 10 Drawing Sheets

(51) Int. Cl.
    *H01L 27/30*     (2006.01)
    *H01L 51/42*     (2006.01)

(52) U.S. Cl.
    CPC ........ *H01L 51/0078* (2013.01); *H01L 27/307* (2013.01); *H01L 51/4253* (2013.01)

(56) References Cited

U.S. PATENT DOCUMENTS

| | | | |
|---|---|---|---|
| 2013/0015547 A1* | 1/2013 | Hamano | H01L 27/307 257/436 |
| 2015/0218184 A1 | 8/2015 | Kitamura et al. | |
| 2016/0056390 A1* | 2/2016 | Kawada | H01L 51/0071 252/500 |
| 2019/0088880 A1* | 3/2019 | Asaka | C08L 25/02 |

FOREIGN PATENT DOCUMENTS

| | | |
|---|---|---|
| JP | 2014-082247 A | 5/2014 |
| JP | 2016-032047 A | 3/2016 |
| WO | 2014/156773 A1 | 10/2014 |
| WO | WO-2017014146 A1 | 1/2017 |

\* cited by examiner

F I G. 1
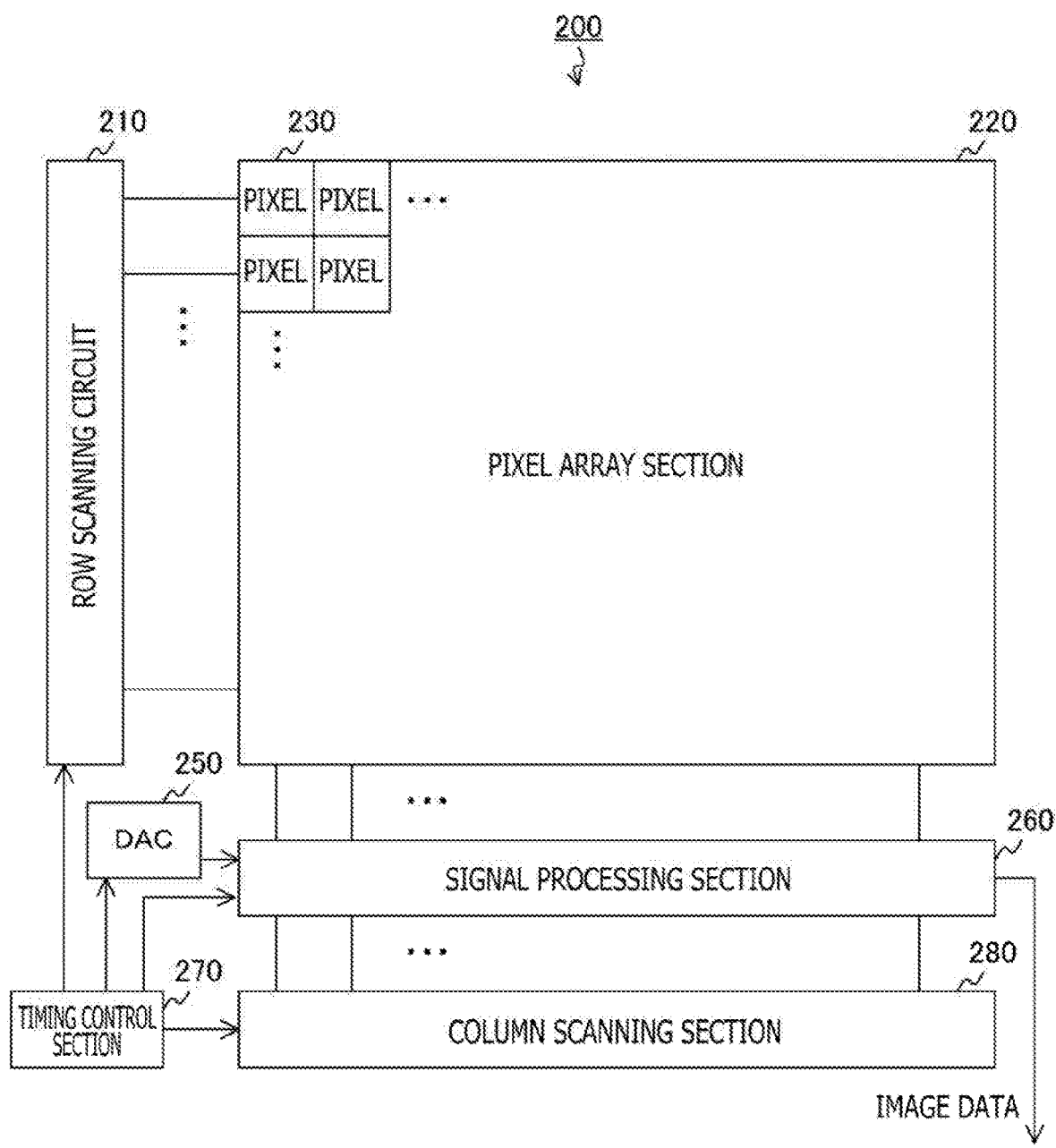

ORGANIC PHOTOELECTRIC CONVERSION ELEMENT

TECHNICAL FIELD

The present technology relates to an organic photoelectric conversion element, and specifically to an organic photoelectric conversion element using organic materials.

BACKGROUND ART

In solid-state imaging devices, photosensor and the like, photoelectric conversion elements have been used to detect light. For the enhancement of the sensitivity of these solid-state imaging devices and photosensors, there is a need to provide photoelectric conversion elements with improved quantum efficiency. Here, quantum efficiency means an efficiency of conversion of photons to electrons. For the enhancement of the operating speed of solid-state imaging devices and photosensors, on the other hand, there is a need to provide photoelectric conversion elements with improved response rate. Now, the term "response rate" means a rate at which the value of a light current measured under illumination of light falls after stopping the illumination of light. For improved quantum efficiency, two methods are effective, one being to provide an element with a bulk-heterostructure, and the other to increase the carrier mobility. For improved response rate, on the other hand, an effective method is to increase the carrier mobility. For example, photoelectric conversion films of a bulk-heterostructure with two kinds of organic materials mixed together have been proposed (for example, see PTL 1).

CITATION LIST

Patent Literature

[PTL 1]
Japanese Patent Laid-Open No. 2002-076391

SUMMARY

Technical Problem

With the above-described conventional technology, however, a photoelectric conversion film cannot be provided with a sufficiently increased carrier mobility because the bulk-heterostructure is inhibited from crystallization and is subjected to amorphization or solution treatment. As a consequence, there is a problem in that the quantum efficiency and response rate can be hardly improved.

The present technology has emerged in view of such circumstances as described above, and has as an object thereof to provide improvements in the quantum efficiency and response rate of a photoelectric conversion element that uses organic materials.

Solution to Problem

The present technology has been made to resolve the above-described problem, and in a first aspect thereof provides an organic photoelectric conversion element including p-type molecules represented by Formula (1) in a photoelectric conversion layer:

[Chem. 1]

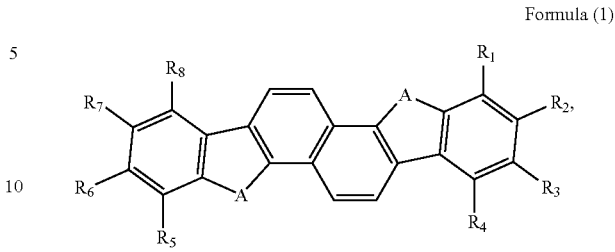

Formula (1)

in which A represents any one of oxygen, sulfur or selenium, any one of $R_1$ to $R_4$ represents a substituted or unsubstituted aryl or heteroaryl having 4 to 30 carbon atoms, the remainder of $R_1$ to $R_4$ each represent hydrogen, any one of $R_5$ to $R_8$ represents a substituted or unsubstituted aryl or heteroaryl having 4 to 30 carbon atoms, and the remainder of $R_5$ to $R_8$ each represent hydrogen. This configuration brings about effects of improvements in the quantum efficiency and response rate of the organic photoelectric conversion element.

In the first aspect, the photoelectric conversion layer may further include n-type molecules, and the n-type molecules may include a fullerene or a fullerene derivative. Owing to this configuration, a bulk heterostructure is formed, thereby bringing about effects of improvements in the quantum efficiency and response rate of the organic photoelectric conversion element.

Further, in the first aspect, the n-type molecules amount to a volume fraction of 10 to 50 percent relative to the photoelectric conversion layer. Owing to this configuration, a bulk heterostructure is formed, thereby bringing about effects of improvements in the quantum efficiency and response rate of the organic photoelectric conversion element.

Further, in the first aspect, the n-type molecules may include the fullerene derivative represented by any one of Formula (2) or (3):

[Chem. 2]

Formula (2)

[Chem. 3]

Formula (3)

and in the Formulae (2) and (3), R independently represents hydrogen, halogen, linear, branched or cyclic alkyl, phenyl, a linear or fused-ring aromatic-containing group, a halogenide-containing group, partial fluoroalkyl, perfluoroalkyl, silylalkyl, silylalkoxy, arylsilyl, arylsulfanyl, alkylsulfanyl, arylsulfonyl, alkylsulfonyl, arylsulfido, alkylsulfido, amino, alkylamino, arylamino, hydroxy, alkoxy, acylamino, acyloxy, carbonyl, carboxy, carboxamido, carboalkoxy, acyl, sulfonyl, cyano, nitro, a chalcogenide-containing group, phosphino or phosphono, or a derivative thereof, and n and m each stand for an integer. Owing to this configuration, a bulk heterostructure is formed, thereby bringing about effects of improvements in the quantum efficiency and response rate of the organic photoelectric conversion element.

In the first aspect, the photoelectric conversion layer may further include a colorant, and the colorant may have a maximum absorption coefficient of not smaller than 50000 cm in a wavelength range of visible light. This configuration brings about an effect of an improvement in the sensitivity of the organic photoelectric conversion element to visible light.

Further, in the first aspect, the colorant may amount to a volume fraction of 20 to 80 percent relative to the photoelectric conversion layer. This configuration brings about an effect of an improvement in the sensitivity of the organic photoelectric conversion element to visible light.

Further, in the first aspect, the colorant may include a subphthalocyanine derivative. This configuration brings about an effect of an improvement in the sensitivity of the organic photoelectric conversion element to visible light.

Further, in the first aspect, the colorant may include a subphthalocyanine derivative represented by Formula (4):

[Chem. 4]

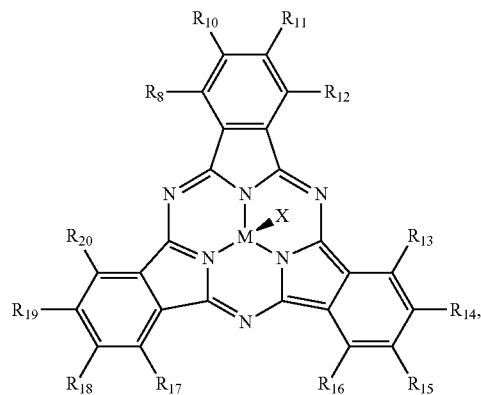

Formula (4)

and $R_9$ to $R_{20}$ in the Formula (4) are each independently selected from a group including hydrogen, halogen, linear, branched or cyclic alkyl, thioalkyl, thioaryl, arylsulfonyl, alkylsulfonyl, amino, alkylamino, arylamino, hydroxy, alkoxy, acylamino, acyloxy, phenyl, carboxy, carboxamido, carboalkoxy, acyl, sulfonyl, cyano and nitro, M represents boron or a divalent or trivalent metal, and X represents an anionic group. This configuration brings about an effect of an improvement in the sensitivity of the organic photoelectric conversion element to visible light.

Further, in the first aspect, the p-type molecules may amount to a volume fraction of 10 to 70 percent relative to the photoelectric conversion layer. This configuration brings about effects of improvements in the quantum efficiency and response rate of the organic photoelectric conversion element.

Further, in the first aspect, the photoelectric conversion layer may include, as the p-type molecules, a compound represented by Formula (9) out of the compounds represented by Formula (1). This configuration brings about effects of improvements in the quantum efficiency and response rate of the organic photoelectric conversion element.

[Chem. 5]

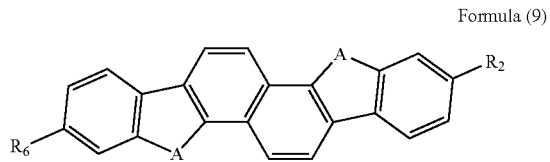

Formula (9)

Further, in the first aspect, the photoelectric conversion layer may include, as the p-type molecules, a compound represented by Formula (10) out of the compounds represented by Formula (9):

[Chem. 6]

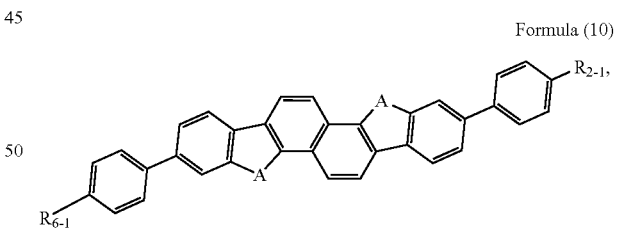

Formula (10)

and in the Formula (10), $R_{2-1}$ and $R_{6-1}$ may each be a substituted or unsubstituted aryl group or heteroaryl group having 4 to 24 carbon atoms. This configuration brings about effects of improvements in the quantum efficiency and response rate of the organic photoelectric conversion element.

Further, in the first aspect, the photoelectric conversion layer includes, as the p-type molecules, a compound represented by Formula (11) out of the compounds represented by Formula (10):

[Chem. 7]

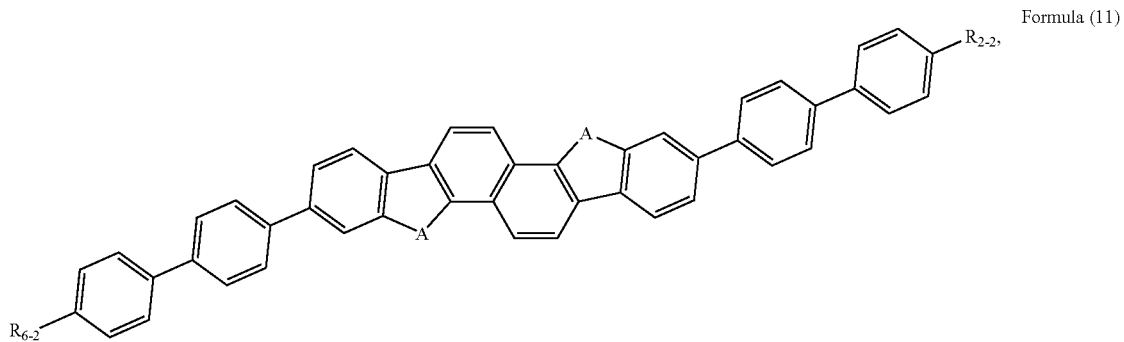

Formula (11)

and in the Formula (11), $R_{2-2}$ and $R_{6-2}$ may each be a substituted or unsubstituted aryl group or heteroaryl group having 4 to 18 carbon atoms. This configuration brings about effects of improvements in the quantum efficiency and response rate of the organic photoelectric conversion element.

Further, in the first aspect, the photoelectric conversion layer may include, as the p-type molecules, a compound represented by Formula (12) out of the compounds represented by Formula (10). This configuration brings about effects of improvements in the quantum efficiency and response rate of the organic photoelectric conversion element.

[Chem. 8]

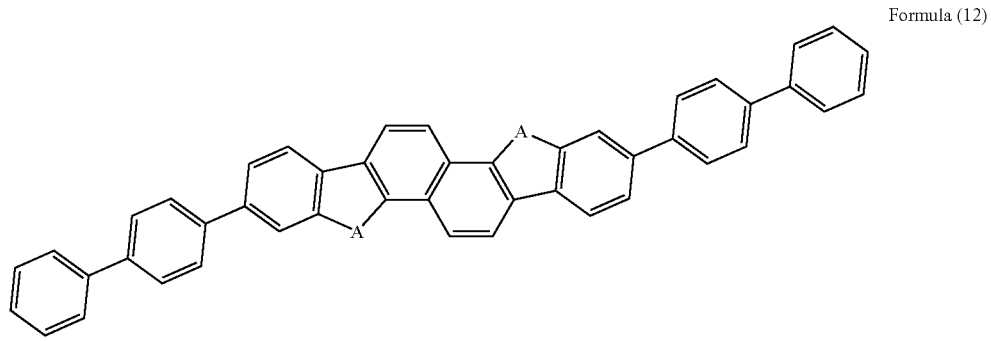

Formula (12)

Further, in the first aspect, the photoelectric conversion layer may include, as the p-type molecules, a compound represented by Formula (13) out of the compounds represented by Formula (12). This configuration brings about effects of improvements in the quantum efficiency and response rate of the organic photoelectric conversion element.

[Chem. 9]

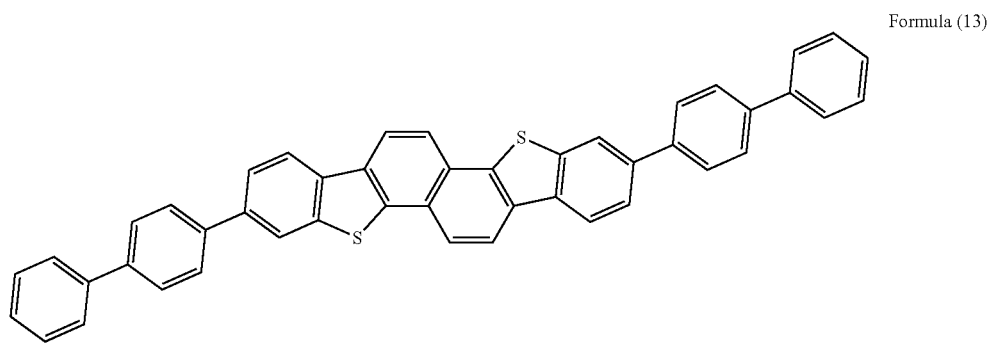

Formula (13)

Further, in the first aspect, the photoelectric conversion layer may include, as the p-type molecules, a compound represented by Formula (15) out of the compounds represented by Formula (1). This configuration brings about effects of improvements in the quantum efficiency and response rate of the organic photoelectric conversion element.

[Chem. 10]

Formula (15)

Further, in the first aspect, the photoelectric conversion layer may include, as the p-type molecules, a compound represented by Formula (16) out of the compounds represented by Formula (15):

[Chem. 11]

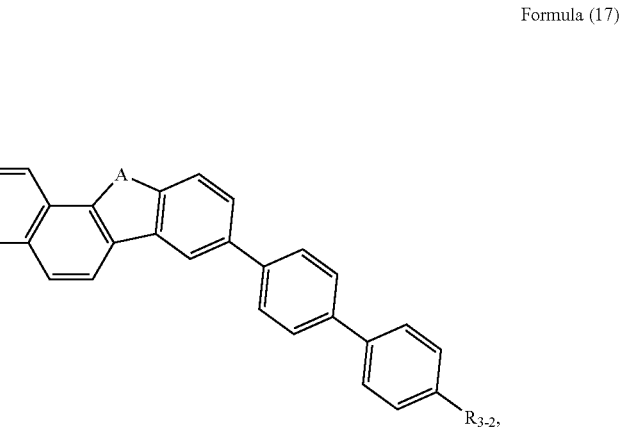

Formula (16)

and in the Formula (16), $R_{3-1}$ and $R_{7-1}$ may each be a substituted or unsubstituted aryl group or heteroaryl group having 4 to 24 carbon atoms. This configuration brings about effects of improvements in the quantum efficiency and response rate of the organic photoelectric conversion element.

Further, in the first aspect, the photoelectric conversion layer may include, as the p-type molecules, a compound represented by Formula (17) out of the compounds represented by Formula (16):

[Chem. 12]

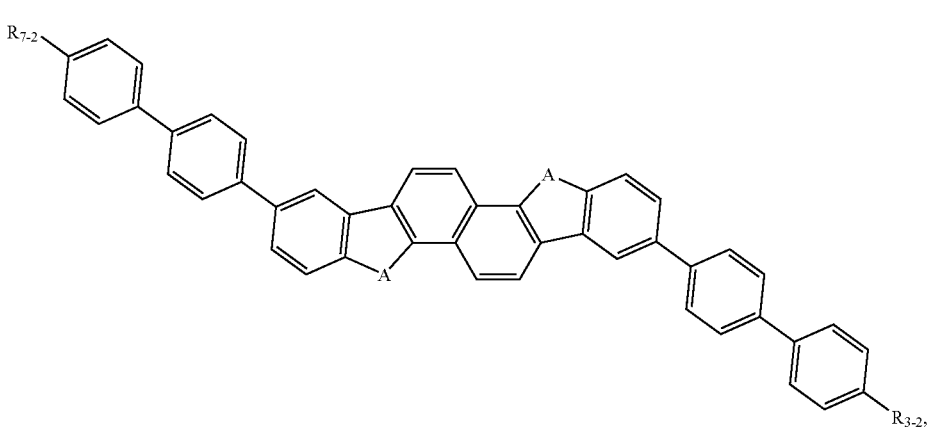

Formula (17)

and in the Formula (17), $R_{3-2}$ and $R_{7-2}$ may each be a substituted or unsubstituted aryl group or heteroaryl group having 4 to 18 carbon atoms. This configuration brings about effects of improvements in the quantum efficiency and response rate of the organic photoelectric conversion element.

Further, in the first aspect, the photoelectric conversion layer may include, as the p-type molecules, a compound represented by Formula (18) out of the compounds represented by Formula (16). This configuration brings about effects of improvements in the quantum efficiency and response rate of the organic photoelectric conversion element.

[Chem. 13]

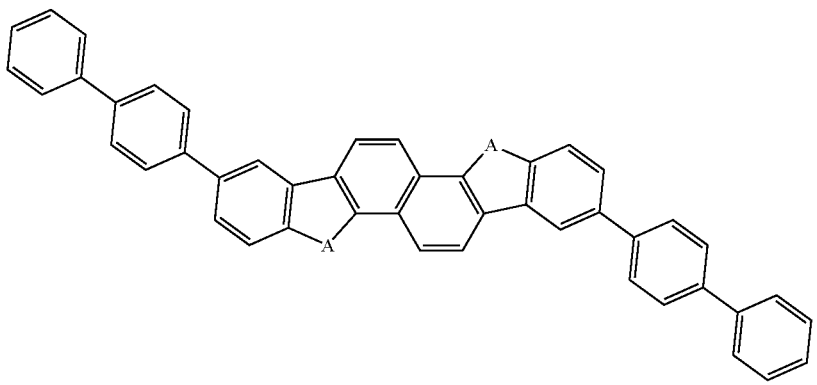

Formula (18)

Further, in the first aspect, the photoelectric conversion layer may include, as the p-type molecules, a compound represented by Formula (19) out of the compounds represented by Formula (18). This configuration brings about effects of improvements in the quantum efficiency and response rate of the organic photoelectric conversion element.

[Chem. 14]

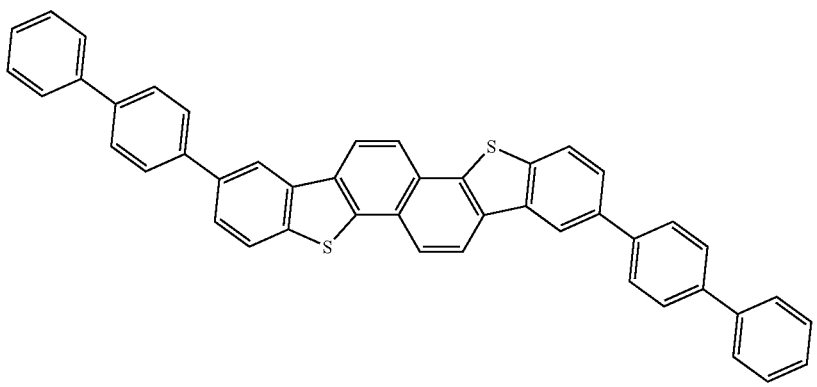

Formula (19)

Further, the present technology also provides, in a second aspect thereof, an organic photoelectric conversion element including p-type molecules represented by Formula (20) in a photoelectric conversion layer:

[Chem. 15]

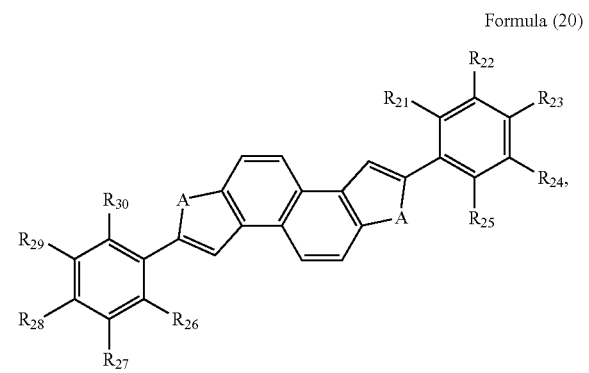

Formula (20)

in which A represents any one of oxygen, sulfur or selenium, any one of $R_{21}$ to $R_{25}$ represents a substituted or unsubstituted aryl or heteroaryl having 4 to 30 carbon atoms, the remainder of $R_{21}$ to $R_{25}$ each represent hydrogen, any one of $R_{26}$ to $R_{30}$ represents a substituted or unsubstituted aryl or heteroaryl having 4 to 30 carbon atoms, and the remainder of $R_{26}$ to $R_{30}$ each represent hydrogen. This configuration brings about effects of improvements in the quantum efficiency and response rate of the organic photoelectric conversion element.

In the second aspect, the photoelectric conversion layer may further include n-type molecules, and the n-type molecules may include a fullerene or a fullerene derivative. Owing to this configuration, a bulk heterostructure is formed, thereby bringing about effects of improvements in the quantum efficiency and response rate of the organic photoelectric conversion element.

Further, in the second aspect, the n-type molecules may amount to a volume fraction of 10 to 50 percent relative to the photoelectric conversion layer. Owing to this configuration, a bulk heterostructure is formed, thereby bringing about effects of improvements in the quantum efficiency and response rate of the organic photoelectric conversion element.

Further, in the second aspect, the n-type molecules may include the fullerene derivative represented by any one of Formula (2) or (3):

[Chem. 16]

Formula (2)

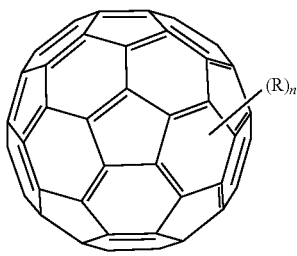

[Chem. 17]

Formula (3)

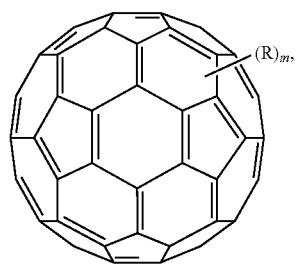

and in the Formulae (2) and (3), R independently represents hydrogen, halogen, linear, branched or cyclic alkyl, phenyl, a linear or fused-ring aromatic-containing group, a halogenide-containing group, partial fluoroalkyl, perfluoroalkyl, silylalkyl, silylalkoxy, arylsilyl, arylsulfanyl, alkylsulfanyl, arylsulfonyl, alkylsulfonyl, arylsulfido, alkylsulfido, amino, alkylamino, arylamino, hydroxy, alkoxy, acylamino, acyloxy, carbonyl, carboxy, carboxamido, carboalkoxy, acyl, sulfonyl, cyano, nitro, a chalcogenide-containing group, phosphino or phosphono, or a derivative thereof, and n and m each stand for an integer. Owing to this configuration, a bulk heterostructure is formed, thereby bringing about effects of improvements in the quantum efficiency and response rate of the organic photoelectric conversion element.

In the second aspect, the photoelectric conversion layer may further include a colorant, and the colorant may have a maximum absorption coefficient of not smaller than 50000 $cm^{-1}$ in a wavelength range of visible light. This configuration brings about an effect of an improvement in the sensitivity of the organic photoelectric conversion element to visible light.

Further, in the second aspect, the colorant may amount to a volume fraction of 20 to 80 percent relative to the photoelectric conversion layer. This configuration brings about an effect of an improvement in the sensitivity of the organic photoelectric conversion element to visible light.

Further, in the second aspect, the colorant may include a subphthalocyanine derivative. This configuration brings about an effect of an improvement in the sensitivity of the organic photoelectric conversion element to visible light.

Further, in the second aspect, the colorant may include a subphthalocyanine derivative represented by Formula (4):

[Chem. 18]

Formula (4)

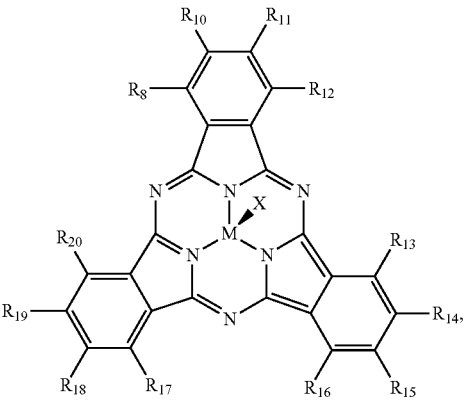

and $R_9$ to $R_{20}$ in the Formula (4) may each be independently selected from a group including hydrogen, halogen, linear, branched or cyclic alkyl, thioalkyl, thioaryl, arylsulfonyl, alkylsulfonyl, amino, alkylamino, arylamino, hydroxy, alkoxy, acylamino, acyloxy, phenyl, carboxy, carboxamido, carboalkoxy, acyl, sulfonyl, cyano and nitro, M represents boron or a divalent or trivalent metal, and X represents an anionic group. This configuration brings about an effect of an improvement in the sensitivity of the organic photoelectric conversion element to visible light.

In the second aspect, the p-type molecules may amount to a volume fraction of 10 to 70 percent relative to the photoelectric conversion layer. This configuration brings about effects of improvements in the quantum efficiency and response rate of the organic photoelectric conversion element.

Advantageous Effect of Invention

According to this technology, it is possible to bring about excellent advantageous effects of improvements in the quantum efficiency and response rate of a photoelectric conversion element that uses organic materials. It is to be noted that advantageous effects described here may not be necessarily limited but any one of advantageous effects described in the present disclosure.

BRIEF DESCRIPTION OF DRAWINGS

FIG. 1 is a block diagram illustrating a configuration example of a solid-state imaging device in a first embodiment of the present technology.

DESCRIPTION OF EMBODIMENTS

Figure 2:
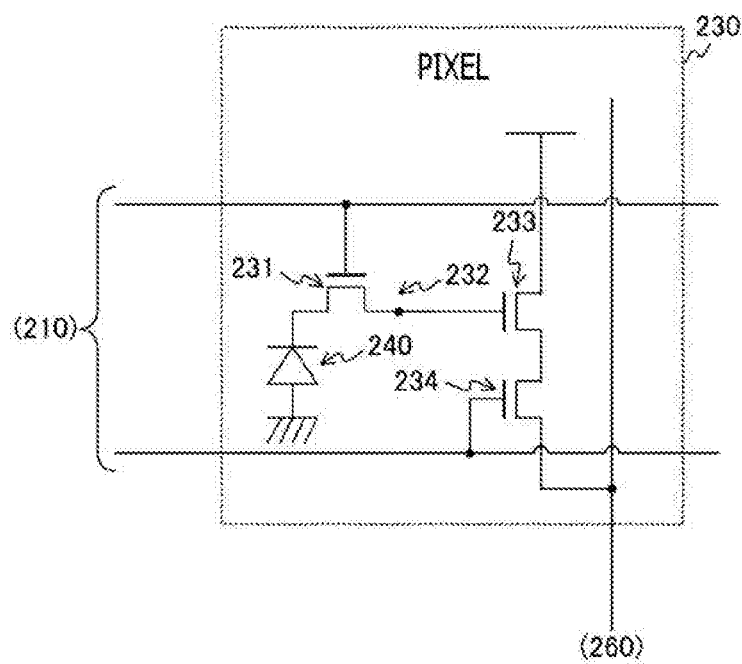
FIG. 2 is a circuit diagram illustrating a configuration example of a pixel in the first embodiment of the present technology.

Modes for practicing the present technology (hereinafter called "embodiments") will hereinafter be described. The description will be made in the following order.
1. First embodiment (an example in which p-type molecules represented by Formula (1) are included in a photoelectric conversion layer)
2. Second embodiment (an example in which p-type molecules represented by Formula (9) are included in a photoelectric conversion layer)

1. First Embodiment

[Configuration Example of Solid-State Imaging Device]
FIG. 1 is a block diagram illustrating a configuration example of a solid-state imaging device 200 in the first embodiment of the present technology. This solid-state imaging device 200 is arranged in an electronic device (personal computer, smartphone, digital camera, or the like) having an imaging function. The solid-state imaging device 200 includes a row scanning circuit 210, a pixel array section 220, a DAC (Digital to Analog Converter) 250, a signal processing section 260, a timing control section 270, and a column scanning circuit 280.

Further, in the pixel array section 220, a plurality of pixels 230 is arranged in a two-dimensional lattice pattern.

The row scanning circuit 210 drives the pixels 230 to output pixel signals. The timing control section 270 controls timings at which the row scanning circuit 210, signal processing section 260 and column scanning circuit 280 operate, respectively. The DAC 250 generates ramp signals by DA (digital-to-analog) conversion, and supplies them to the signal processing section 260.

The signal processing section 260 performs signal processing such as AD (analog-to-digital) conversion on pixel signals to generate pixel data. The column scanning circuit 280 controls the signal processing section 260 to output pixel data.

[Configuration Example of Pixel]
FIG. 2 is a circuit diagram illustrating a configuration example of the pixel 230 in the first embodiment of the present technology. The pixel 230 includes an organic photoelectric conversion element 240, a transfer transistor 231, a floating diffusion layer 232, an amplifier transistor 233, and a selection transistor 234.

The organic photoelectric conversion element 240 photoelectrically converts incident light to generate electric charges. The transfer transistor 231 acts to transfer the electric charges from the organic photoelectric conversion element 240 to the floating diffusion layer 232 according to transfer signals from the row scanning circuit 210.

The floating diffusion layer 232 acts to accumulate electric charges, and to generates voltages according to the quantities of the electric charges so accumulated. The amplifier transistor 233 acts to amplify the voltages from the floating diffusion layer 232, and to generate analog pixel signals. The selection transistor 234 acts to output pixel signals to the signal processing section 260 according to selection signals from the row scanning circuit 210.

It is to be noted that the organic photoelectric conversion element 240 is arranged in the solid-state imaging device 200 but may also be arranged in a circuit or device other than the solid-state imaging device 200. For example, the organic photoelectric conversion element 240 can also be arranged in a ToF (time-of-flight) sensor or in a line sensor that detects phase differences.

Figure 3:
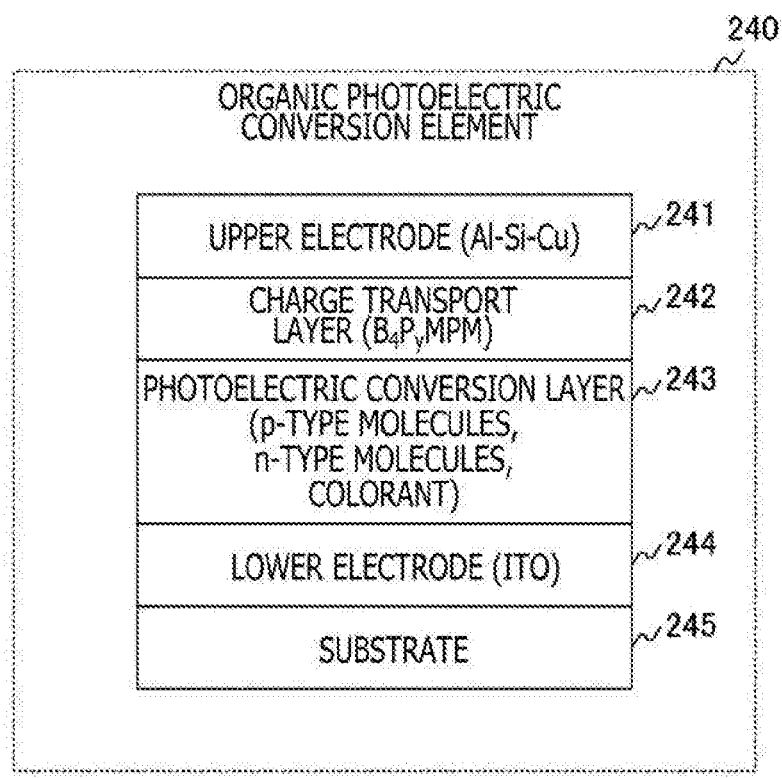
FIG. 3 is a diagram illustrating a configuration example of an organic photoelectric conversion element in the first embodiment of the present technology.

[Configuration Example of Organic Photoelectric Conversion Element]
FIG. 3 is a diagram illustrating a configuration example of the organic photoelectric conversion element 240 in the first embodiment of the present technology. This organic photoelectric conversion element 240 includes an upper electrode 241, a charge transport layer 242, a photoelectric conversion layer 243, a lower electrode 244, and a substrate 245.

As the material of the substrate 245, quartz glass is used, for example. Taking, as an upward direction, the direction from the substrate 245 to the upper electrode 241, the lower electrode 244 is formed over the substrate 245. As the material of the lower electrode 244, indium tin oxide (ITO) is used, for example.

Over the lower electrode 244, the photoelectric conversion layer 243 is formed. This photoelectric conversion layer 243 includes p-type molecules represented by Formula (1), n-type molecules, and a colorant.

[Chem. 19]

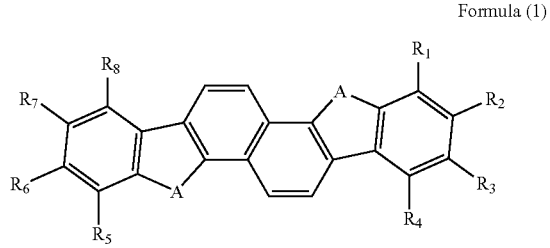

Formula (1)

in which A represents any one of oxygen (O), sulfur (S) or selenium (Se), any one of $R_1$ to $R_4$ represents a substituted or unsubstituted aryl or heteroaryl having 4 to 30 carbon atoms, the remainder of $R_1$ to $R_4$ each represent hydrogen (H), any one of $R_5$ to $R_8$ represents a substituted or unsubstituted aryl or heteroaryl having 4 to 30 carbon atoms, and the remainder of $R_5$ to $R_8$ each represent hydrogen (H).

Here, the term "substituted or unsubstituted" means that a compound may have one or more of various desired substituents in place of a like number of hydrogen atoms in the compound or may have none of such substituents.

Further, as the positions of substitution by aryl groups or heteroaryl groups in Formula (1), the combination of $R_2$ and $R_6$ or the combination of $R_3$ and $R_7$ is desired for the reason that a linear, fused-ring molecule of high planarity like Formula (1) is known to have a herringbone crystal structure and to form a two-dimensional carrier transport path and the molecular shape is desirably linear in order to have such a crystal structure. The selection of aryl groups or heteroaryl groups for either $R_2$ and $R_6$ or $R_3$ and $R_7$ allows the positions of substitution to be linear.

For a similar reason, even if each aryl group is not single but is connected to a biphenyl group or a terphenyl group, each ring of the aryl group is desirably connected at the para position thereof to the biphenyl or terphenyl group from the viewpoint of providing linearity. If a five-membered ring such as a bithienyl group or terthienyl group is connected to an aryl group or a heteroaryl group, the connection via the carbon at the alpha position of the thiophene ring is desired for higher linearity. Further, if each aryl group or each heteroaryl group includes a fused multi-ring group such as naphthalene ring, benzothiophene ring or indole ring, they are desirably connected to provide high linearity.

The substituents of $R_1$ to $R_4$ and of $R_5$ to $R_8$ are desirably the same, and in addition the symmetry of the positions of substitution is desirably twofold symmetry, for the reason that, in a case of having a crystal structure, higher symmetry leads to smaller anisotropy and to a smaller band dispersion width.

Now, for the realization of high quantum efficiency and response rate in an organic photoelectric conversion element, it is effective to have a bulk-heterostructure and also to increase the carrier mobilities of respective organic materials. The term "bulk-heterostructure" means that an electron-donating, organic semiconductor material and an electron-accepting, organic semiconductor material are separated in different phases on a nanometer scale. Owing to such a bulk-heterostructure, it is possible to shorten the distance over which excitons generated under illumination of light move to a donor/acceptor interface, so that the dissociation efficiency of excitons into holes and electrons is increased. Further, this improved carrier mobility can increase the efficiency that the resulting holes and electrons reach respective electrodes without recombination. For an increase in this carrier mobility, the organic semiconductor is desirably crystalline, because a regular structure leads to a greater overlap between adjacent molecular orbitals and hence to a higher probability of hopping and a higher carrier transfer rate. For the realization of an organic photoelectric conversion element having high quantum efficiency and response rate, there is a need for materials that exhibit a high carrier mobility for crystallization while undergoing phase separation on a nanometer scale owing to its bulk-heterostructure. The compound of Formula 1 is a p-type material that satisfies these conditions.

On the other hand, the n-type molecules include, for example, at least one fullerene or fullerene derivative. As the fullerene derivative, a compound represented by Formula (2) or formula (3) is used, for example:

[Chem. 20]

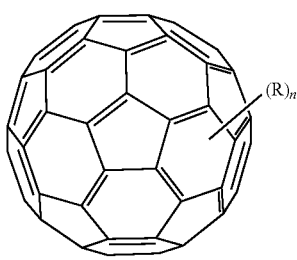

Formula (2)

[Chem. 21]

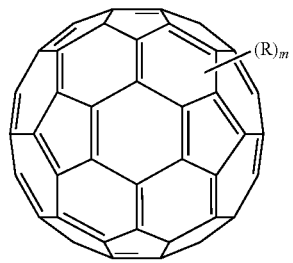

Formula (3)

in which R independently represents hydrogen, halogen, linear, branched or cyclic alkyl, phenyl, a linear or fused-ring aromatic-containing group, a halogenide-containing group, partial fluoroalkyl, perfluoroalkyl, silylalkyl, silylalkoxy, arylsilyl, arylsulfanyl, alkylsulfanyl, arylsulfonyl, alkylsulfonyl, arylsulfido, alkylsulfido, amino, alkylamino, arylamino, hydroxy, alkoxy, acylamino, acyloxy, carbonyl, carboxy, carboxamido, carboalkoxy, acyl, sulfonyl, cyano, nitro, a chalcogenide-containing group, phosphino or phosphono, or a derivative thereof, and n and m each stand for an integer.

Further, the colorant has a maximum absorption coefficient of not smaller than 50000 $cm^{-1}$ in a wavelength range of visible light (for example, 400 to 750 nm). As this colorant, a subphthalocyanine derivative represented by Formula (4) is used, for example:

[Chem. 22]

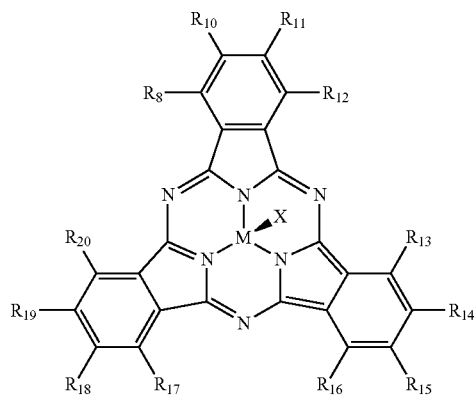

Formula (4)

in which $R_9$ to $R_{20}$ are each independently selected from the group including hydrogen, halogen, linear, branched or cyclic alkyl, thioalkyl, thioaryl, arylsulfonyl, alkylsulfonyl, amino, alkylamino, arylamino, hydroxy, alkoxy, acylamino, acyloxy, phenyl, carboxy, carboxamido, carboalkoxy, acyl, sulfonyl, cyano and nitro, M represents boron or a divalent or trivalent metal, and X represents an anionic group. Examples of this anionic group include halogen, cyano, alkoxy (including alkoxy groups in alkyl compounds, polycyclic aromatic hydrocarbons, and heteroring-containing compounds), and phenoxy.

It is to be noted that in Formula (4), desired adjacent ones of $R_9$ to $R_{20}$ may each be a moiety of a fused aliphatic ring or fused aromatic ring. Further, the fused aliphatic ring or fused aromatic ring may contain one or a plurality of non-carbon atoms.

Furthermore, the p-type molecules amount to a volume proportion, that is, a volume fraction of 10 to 70 percent (%) relative to the photoelectric conversion layer 243. On the other hand, the colorant amounts to a volume fraction of 20 to 80 percent (%) relative to the photoelectric conversion layer 243, and the n-type molecules amount to a volume fraction of 10 to 50 percent relative to the photoelectric conversion layer 243. The proportions of the p-type molecules, colorant and n-type molecules are set, for example, at 3:3:2 so that these conditions are satisfied.

Over the photoelectric conversion layer 243, the charge transport layer 242 is formed. As the material of the charge transport layer 242, bis-3,6-(3,5-di-4-pyridylphenyl)-2-methylpyrimidine (hereinafter abbreviated as "B4PyMPM") is used, for example.

Over the charge transport layer 242, the upper electrode 241 is formed. As the material of the upper electrode 241, an electrode material, for example, a transparent conductive metal oxide semiconductor of indium tin oxide (ITO) or indium zinc oxide (IZO) is desired. As an alternative, a metal electrode of Al, an Al—Si—Cu alloy, Cu, Ag or Au may also be used.

[Fabrication Method of Organic Photoelectric Conversion Element]

A simplistic description will next be made about a fabrication method of the organic photoelectric conversion element 240. First, the substrate 245 with the lower electrode 244 formed thereover was cleaned by ultraviolet (UV)/ozone treatment, and the substrate 245 was transferred into a vacuum deposition machine. With the pressure reduced to $1 \times 10^{-5}$ Pascal (Pa) inside the vacuum deposition machine, the photoelectric conversion layer 243 that included the p-type molecules of Formula (1), the colorant of Formula (4) and the n-type molecules (fullerene or the like) was deposited to 200 nanometer (nm) while rotating a substrate holder. The deposition rates of the p-type molecules, colorant and n-type molecules are, for example, 0.75 angstrom/sec, 0.75 angstrom/sec and 0.50 angstrom/sec, respectively.

Subsequently, B4PyMPM was deposited to 5 nanometer (nm) at a deposition rate of 0.3 angstrom/sec to form the charge transport layer 242. Finally, an Al—Si—Cu alloy was vapor deposited with a thickness of 100 nanometer to form the upper electrode 241. By those procedures, the organic photoelectric conversion element 240 was fabricated with a light-receiving area of 1 millimeter (mm) square.

Example 1

A description will next be made about Example 1 in the first embodiment. In Example 1, p-type molecules were prepared according to the following reaction scheme:

Scheme (5)

[Chem. 23]

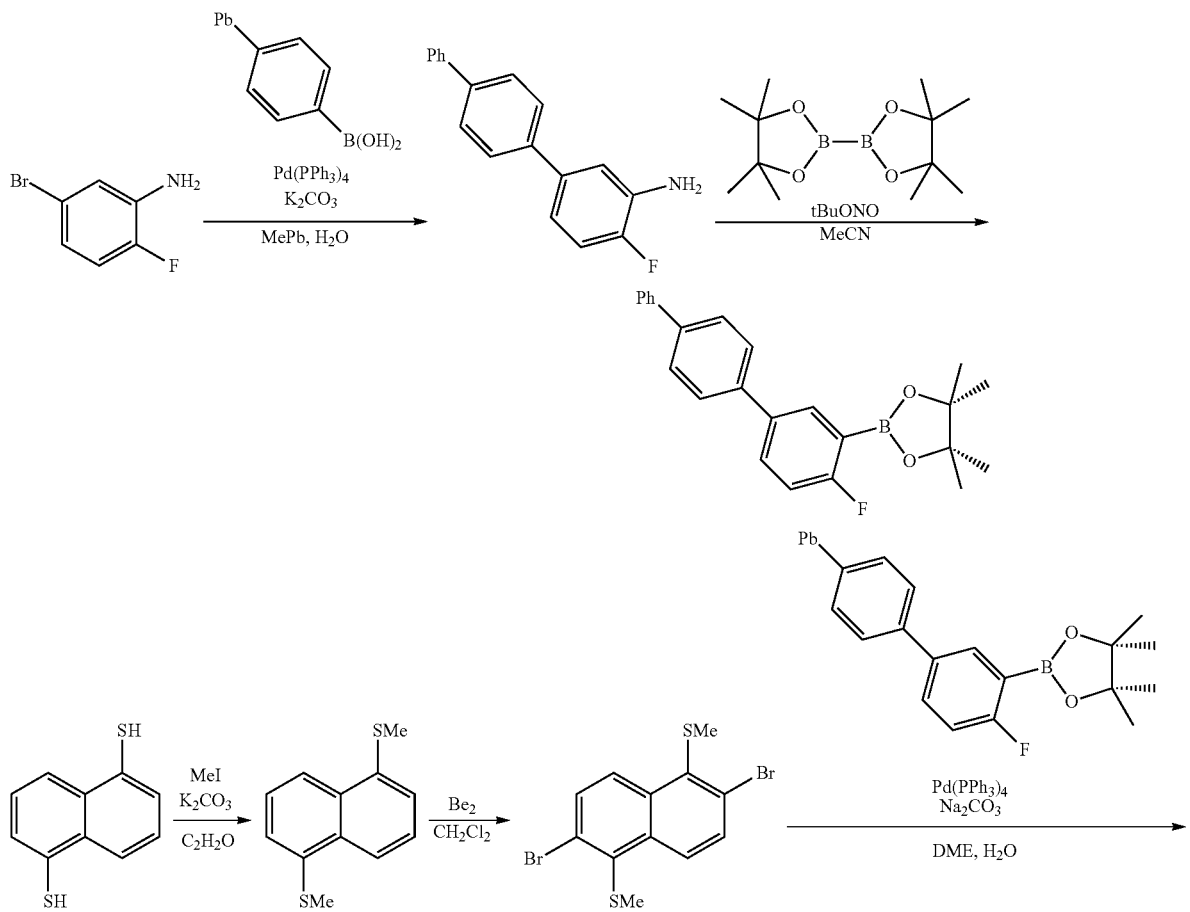

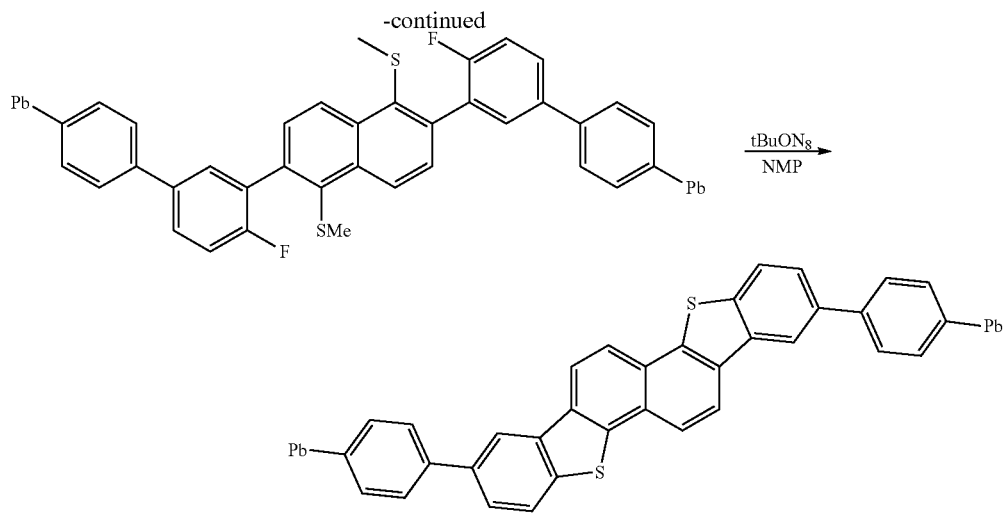

In Scheme (5), the synthesis of the compound (b) was conducted with reference to Paragraph [0145] in the specification of US Patent Application Publication No. 2013/0228752. Described specifically, under an argon (Ar) atmosphere in a four-necked flask, 5-bromo-2-fluoroaniline, 4-biphenylboronic acid, potassium carbonate and Pd(PPh$_3$)$_4$ were refluxed with heating in a mixed solution of distilled water and toluene. Here, the chemical equivalents of 5-bromo-2-fluoroaniline, 4-biphenylboronic acid, potassium carbonate and Pd(PPh$_3$)$_4$ were "1," "1," "2.6" and "0.0180," respectively. After allowed to cool at room temperature, the precipitated solid was collected by filtration, dissolved in chloroform, and collected by filtration on silica gel. As a result, the compound (b) was obtained as a white solid with a yield of approximately 62 percent (%).

The synthesis of the compound (c) was next conducted with reference to Scheme (4) of Qiu D., et al., "Synthesis of pinacol arylboronates from aromatic amines: a metal-free transformation," J. Org. Chem., 2013, 78, 1923-1933. Described specifically, under an argon (Ar) atmosphere in a Schlenk flask, the compound (b), bis(pinacolato)diboron and tert-butyl nitrite were stirred at 80° C. over 2 hours in acetonitrile. Here, the chemical equivalents of the compound (b), bis(pinacolato)diboron and tert-butyl nitrite were "1," "1.2" and "2.4," respectively. After allowed to cool at room temperature, the precipitated solid was collected by filtration, the resulting solid was dissolved in dichloromethane, the resulting solution was filtered through silica gel, and the filtrate was concentrated. As a result, the compound (c) was obtained as a creamy yellow solid with a yield of approximately 40 percent (%).

The synthesis of the compound (e) was next conducted with reference to Scheme 3 in Toyoshi Shimada, et al., "Nickel-Catalyzed Asymmetric Grignard Cross-Coupling of Dinaphthothiophene Giving Axially Chiral 1,1'-Binaphthyls," J. Org. Chem. J. Am. Chem. Soc., 2002, 124, 13396-13397. Described specifically, under an argon (Ar) atmosphere in a 4-necked flask, 1,5-dimethylcaptonaphthalene, potassium carbonate and methyl iodide were stirred overnight at room temperature in acetone. Here, the chemical equivalents of 1,5-dimethylcaptonaphthalene, potassium carbonate and methyl iodide were "1," "6" and "2," respectively. Distilled water (500 milliliter (mL)) was then added to the reaction suspension, and the precipitated solid was collected by filtration, followed by purification. As a result, the compound (e) was obtained as a pale yellow solid with a yield of approximately 79%.

Through a bromination reaction, the compound (f) was then synthesized from the compound (e). Further, the compound (g) was synthesized from the compound (f) through the Suzuki-Miyaura coupling reaction, followed by the synthesis of the compound (h) from the compound (g) through a cyclization reaction. The compound (h) was used as p-type molecules. The compound (h) in Scheme (5) was an example of the compound of Formula (1).

Further, "NANOM PURPLE SUH" (product of Frontier Carbon Corporation) was used as n-type molecules of fullerene in Example 1. The fullerene was a product purified by sublimation, and had an HPLC (High Performance Liquid Chromatography) purity of higher than 99.9 percent (%).

Furthermore, the colorant was synthesized through the following reaction scheme with reference to Paragraphs [0084] to [0088] in Japan Patent Application No. 2014-099816 (Japan Patent Laid-open No. 2015-233117), and the resulting compound was subjected to purification by sublimation.

Scheme (6)

[Chem. 24]

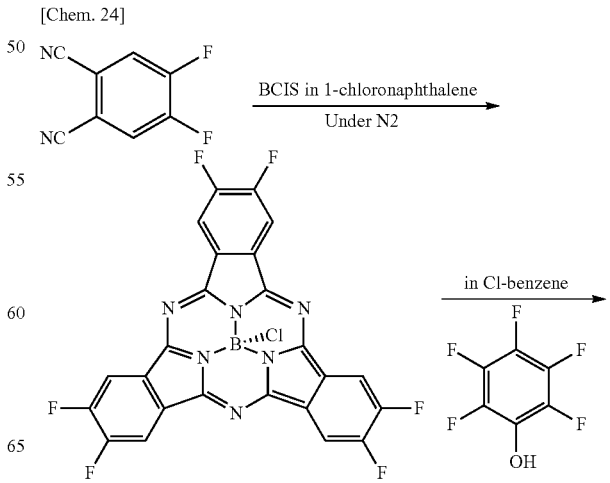

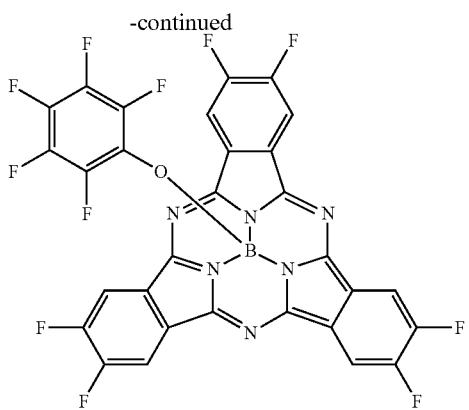

In addition, as B4PyMPM, the compound represented by the following formula was used.

[Chem. 25]

Formula (7)

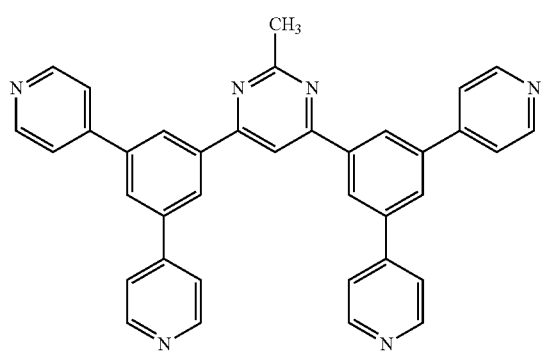

Comparative Example 1

A description will next be made about Comparative Example 1 in the first embodiment. In Comparative Example 1, a quinacridone derivative, specifically, butyl quinacridone (hereinafter, abbreviated as "BQD") represented by Formula (8) was used as p-type molecules.

[Chem. 26]

Formula (8)

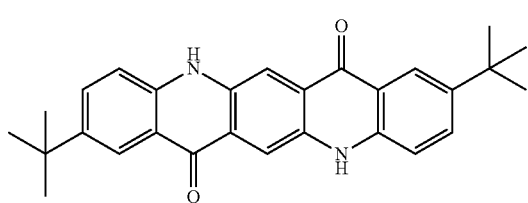

In Comparative Example 1, the production processes of the parts other than the p-type molecules were similar those in Example 1.

[Characteristics of Photoelectric Conversion Element]

A description will next be made about evaluation methods for characteristics of the organic photoelectric conversion element according to Example 1 and those of the organic photoelectric conversion element according to Comparative Example 1. The photoelectric conversion elements or photoelectric conversion layers in Example 1 and Comparative Example 1 were each evaluated for external quantum efficiency, dark current, response rate, crystallinity and hole mobility. In addition, monolayer films of the p-type materials used in Example 1 and Comparative Example 1 were evaluated for crystallinity and hole mobility.

The evaluation of dark current was conducted as will be described next. In a dark state, a bias voltage to be applied between the electrodes of each organic photoelectric conversion element was controlled using a semiconductor parameter analyzer. Setting the voltage of the upper electrode at "−2.6" volt (V) relative to that of the lower electrode, a dark current value was measured.

In the evaluation of external quantum efficiency, light was illuminated to each organic photoelectric conversion element from a light source through a filter. The wavelength of the light was 565 nanometer (nm), and the quantity of the light was 1.62 microwatt per centimeter ($\mu W/cm^2$). On the other hand, a bias voltage to be applied between the electrodes of the organic photoelectric conversion element was controlled using a semiconductor parameter analyzer. The voltage of the upper electrode was "−2.6" volt (V) relative to that of the lower electrode. Under those conditions, measurements were made for the value of light current and the value of dark current. From the difference between the value of light current and the value of dark current and the quantity of received light, the external quantum efficiency was calculated.

In the evaluation of response rate, a measurement was made for a rate at which the value of a light current measured by a semiconductor parameter analyzer during illumination of light fell after stopping the illumination of light. Described specifically, the quantity of light to be illuminated to each photoelectric conversion element from a light source through a filter was set at 1.62 $\mu W/cm^2$, and the bias voltage to be applied between the electrodes was set at −2.6 V. After a measurement was made for steady-state current in the above-described state, the rate at which the current progressively decayed after stopping the illumination of light was set as an indicator for response characteristics. Comparisons will hereinafter be made in terms of standardized response rate with the response rate in Example 1 being assumed to be 1.

The evaluation of crystallinity was made on the monolayer films of the p-type materials used in Example 1 and Comparative Example 1 and the photoelectric conversion layers used in Example 1 and Comparative Example 1. The monolayer films were each formed as will be described hereinafter. A glass substrate was cleaned by UV/ozone treatment, and then transferred into a vacuum deposition machine. With the pressure reduced to 1×10-5 Pa inside the vacuum deposition machine, p-type molecules of Formula (1) or p-type molecules of Formula (8) were deposited to 40 nm while rotating a substrate holder, whereby the monolayer film was obtained. On the photoelectric conversion layers 243 used in Example 1 and Comparative Example 1, X-ray diffractometry was performed by an X-ray diffractometer. As an X-ray, a Cu K-alpha beam is used, for example. By an analysis of X-ray diffraction patterns so obtained, the photoelectric conversion layers 243 were determined for the presence or absence of crystallinity.

Further, in the evaluation of hole mobility, hole mobility evaluation elements were fabricated, in addition to the organic photoelectric conversion elements 240, using photoelectric conversion layers of Example 1 and Comparative Example 1, respectively. In addition, hole mobility evaluation elements were fabricated using monolayer films of the p-type materials that were employed in Example 1 and Comparative Example 1, respectively.

Figure 4:
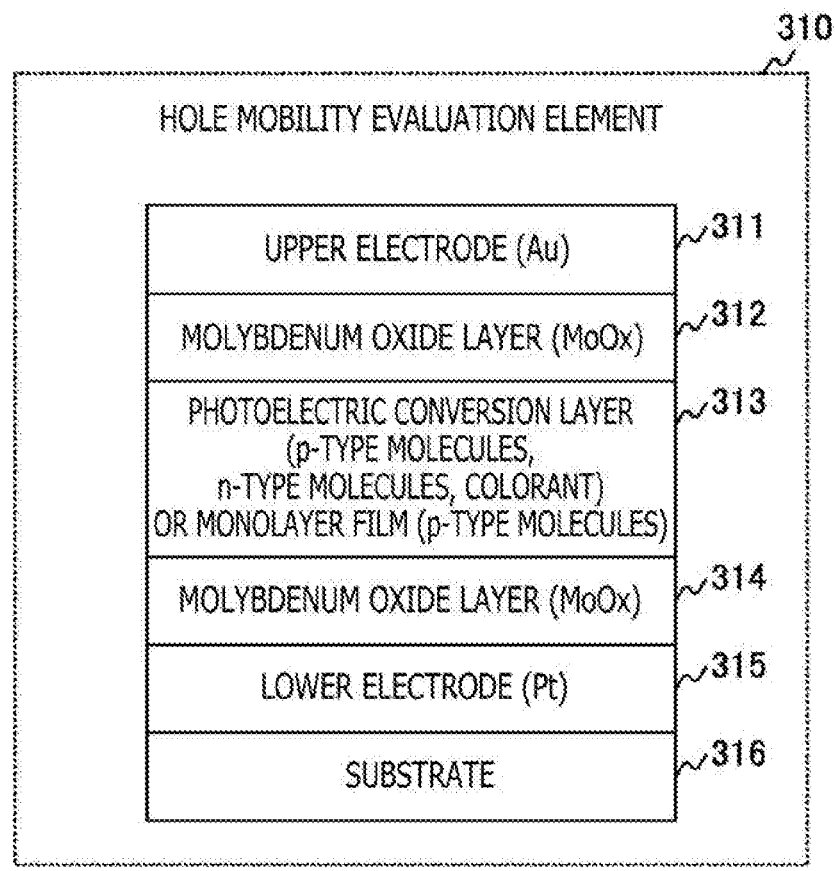
FIG. 4 is a diagram illustrating a configuration example of a hole mobility evaluation element in the first embodiment of the present technology.

FIG. 4 is a diagram illustrating a configuration example of the hole mobility evaluation element 310 in the first embodiment of the present technology. Over a glass substrate 316 with a 50 nanometer (nm) thick, lower electrode 315 of platinum (Pt) arranged thereon, a molybdenum oxide layer 314 of molybdenum trioxide ($MoO_3$) or the like was deposited with a thickness of 0.8 nanometer (nm). Subsequently, similar to the fabrication of the organic photoelectric conversion element 240, p-type molecules, a colorant and n-type molecules (fullerene or the like) were deposited until their mixed layer (photoelectric conversion layer 313) grew to a thickness of 150 nanometer (nm). Here, the deposition rates of the p-type molecules, colorant and n-type molecules are, for example, 0.75 angstrom/sec, 0.75 angstrom/sec and 0.50 angstrom/sec, respectively.

A molybdenum oxide layer 312 of molybdenum trioxide ($MoO_3$) or the like was next deposited with a thickness of 3 nanometer (nm), followed by deposition of an upper electrode 311 of gold (Au) with a thickness of 100 nanometer (nm). As a result, the hole mobility evaluation element 310 was obtained with a light-receiving area of 1 millimeter (mm) square. In the photoelectric conversion layer 313, the p-type molecules, colorant and n-type molecules were set at a ratio of 4:4:2, for example.

As the hole mobility evaluation element for each monolayer film, an element which is configured by substituting, for the photoelectric conversion layer, a monolayer film formed by depositing only p-type molecules, for example, at 1.00 angstrom per second to a thickness of 150 nanometer (nm) is used.

In the evaluation of hole mobility, a bias voltage to be applied between the electrodes was swept from 0 volt (V) to 10 volt (V) by using a semiconductor parameter analyzer, whereby a current-voltage curve was acquired. By fitting the curve to a space charge-limited current model, a relational expression was determined between hole mobility and voltage, and the value of hole mobility at 1 volt (V) was calculated.

Figure 5:
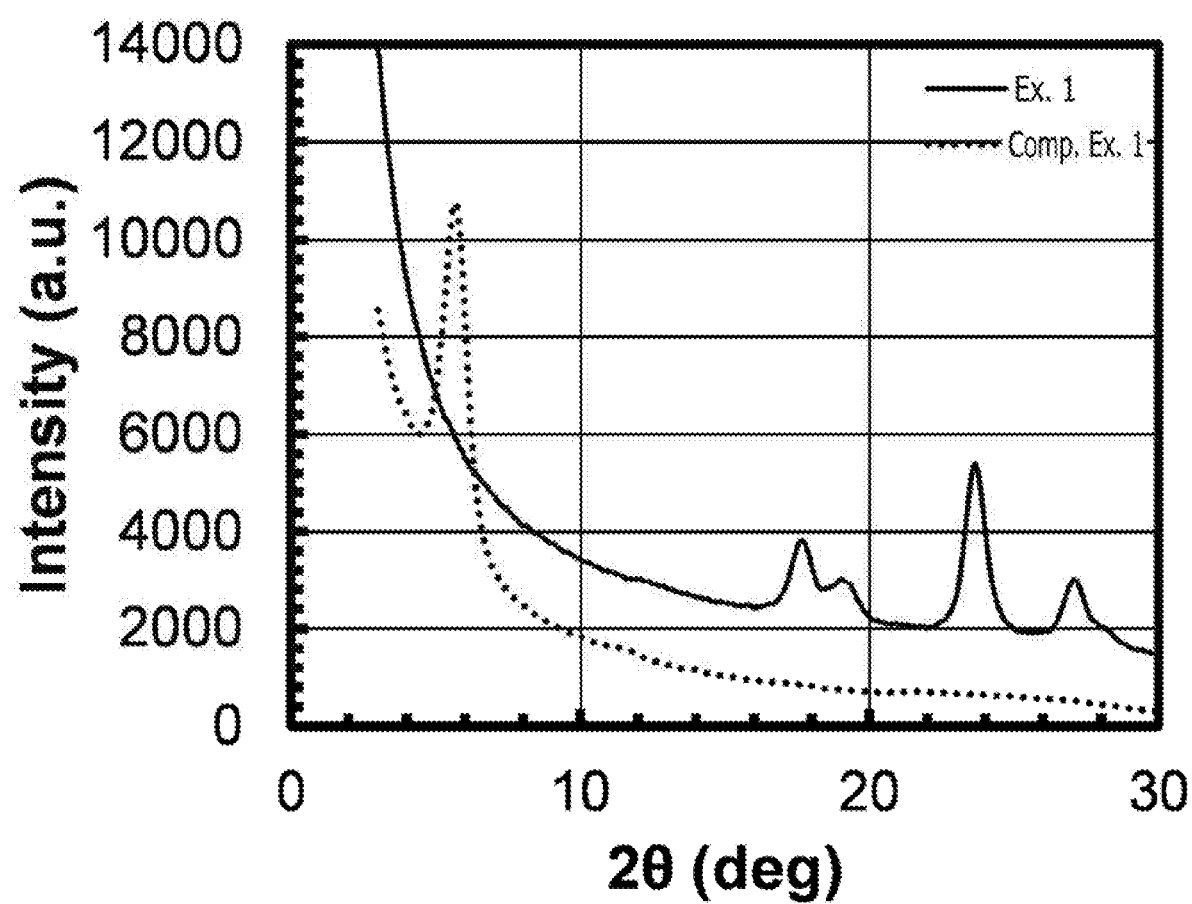
FIG. 5 is a graph illustrating an example of results of X-ray diffractometry of a monolayer film of p-type molecules in Example 1 of the first embodiment of the present technology.
Figure 6:
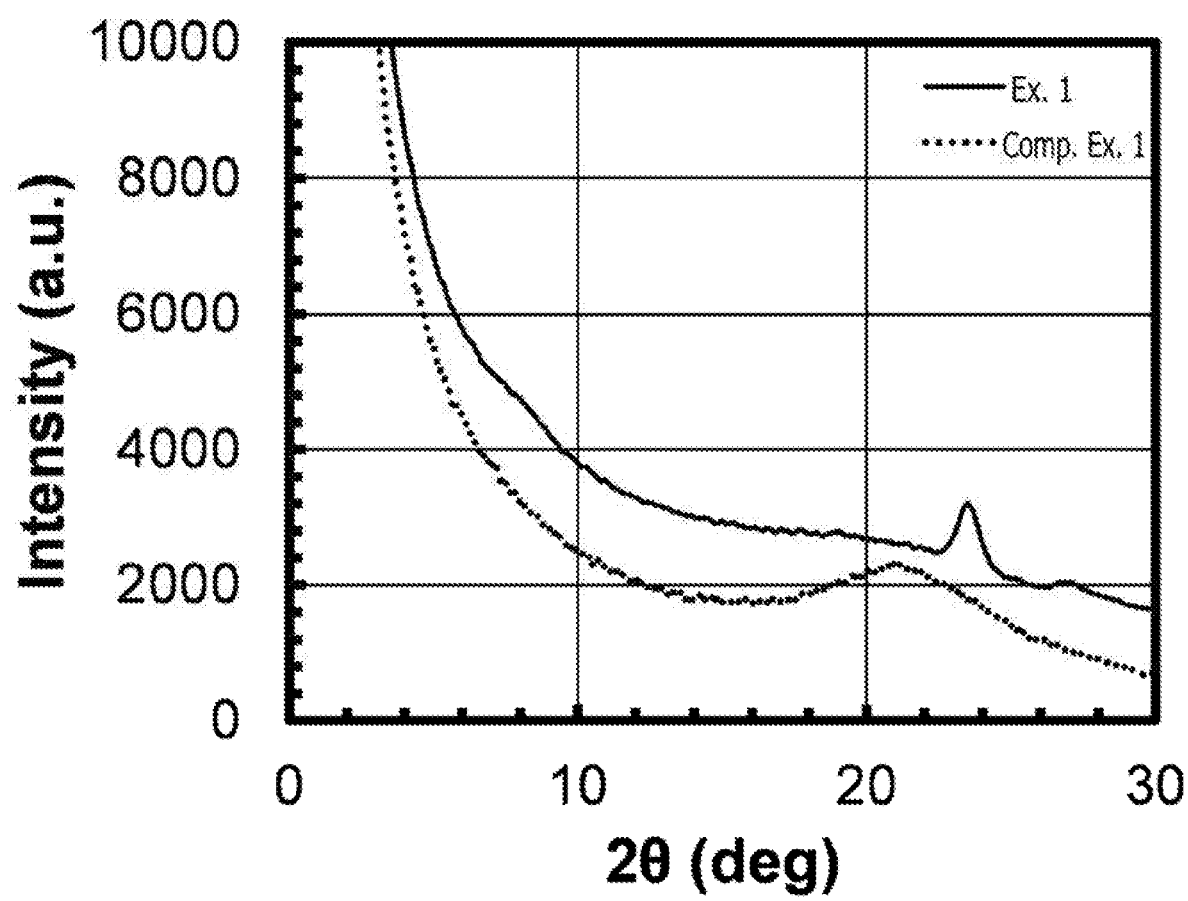
FIG. 6 is a graph illustrating an example of results of X-ray diffractometry of a photoelectric conversion layer in Example 1 of the first embodiment of the present technology.

FIGS. 5 and 6 are graphs illustrating examples of results of X-ray diffractometry in Example 1 in the first embodiment of the present technology. In these figures, the axis of ordinates represents X-ray diffraction intensity, and the axis of abscissas represents diffraction angle. FIG. 5 illustrates the results of X-ray diffractometry of monolayer films of p-type molecules, and FIG. 6 illustrates results of X-ray diffractometry of photoelectric conversion layers. Solid-line loci represent the diffraction results of Example 1, and dotted-line loci represent the diffraction results of Comparative Example 1. As exemplified in FIG. 5, the p-type molecular monolayer films used in Example 1 and Comparative Example 1 each produced peaks in X-ray diffraction intensity, and were each crystalline. As exemplified in FIG. 6, on the other hand, a peak was produced in X-ray diffraction intensity from the photoelectric conversion layer of Example 1, but no peak was produced from the photoelectric conversion layer of Comparative Example 1. It is therefore possible to determine that crystallinity is present in the photoelectric conversion layer of Example 1 while crystallinity is absent in the photoelectric conversion layer of Comparative Example 1. Here, in the determination of the presence or absence of crystallinity, crystallinity was determined to be present if there was a peak having a peak intensity higher by 5 times or greater than the noise level of the base line and a shape with a half-width value of smaller than 1°.

The evaluation results of the individual characteristics in Example 1 and Comparative Example 1 are presented in the following table.

TABLE 1

|  | First embodiment: Ex. 1 | Comp. Ex. 1 |
|---|---|---|
| p-Type molecules | Compound (h) in Scheme (5) | Formula (8) |
| External quantum efficiency (%) | 80 | 77 |
| Dark current (A/cm$^2$) | 1.0E-10 | 3.0E-10 |
| Standardized response rate (a.u.) | 1 | 10 |
| Hole mobility through monolayer (cm$^2$/V · s) | 1.4E-06 | 8.1E-08 |
| Monolayer crystallinity | Present | Present |
| Hole mobility through photoelectric conversion layer (cm$^2$/V · s) | 1.9E-05 | 1.5E-09 |
| Crystallinity of photoelectric conversion layer | Present | Absent |

The external quantum efficiency, dark current and standardized response rate of the photoelectric conversion element in Example 1 were 80 percent (%), 1.0E-10 ampere per square centimeter (A/cm$^2$) and 1. The monolayer of the p-type molecules used in Example 1 had crystallinity, and its SCLC (Space-Charge-Limited Current) mobility (in other words, hole mobility) was 1.4E-6 square centimeter per volt-second (cm$^2$/V·s). The photoelectric conversion layer in the photoelectric conversion element in Example 1 had crystallinity, and the SCLC (hole mobility) of the photoelectric conversion layer was 1.9E-5 square centimeter per volt-second (cm$^2$/V·s).

On the other hand, the external quantum efficiency, dark current and standardized response rate of the photoelectric conversion element in Comparative Example 1 were 77 percent (%), 3.0E-10 ampere per square centimeter (A/cm$^2$) and 10. The monolayer of the p-type molecules used in Comparative Example 1 had crystallinity, and its SCLC mobility (hole mobility) was 8.1E-8 square centimeter per volt-second (cm$^2$/V·s). The photoelectric conversion layer in the photoelectric conversion element of Comparative Example 1 had non-crystallinity, and the SCLC mobility (hole mobility) of the photoelectric conversion layer was 1.5E-9 square centimeter per volt-second (cm$^2$/V·s).

As appreciated from the foregoing, the quantum efficiency and standardized response rate of the organic photoelectric conversion element in Example 1 are higher than those of Comparative Example 1. This is presumably attributable to the fact that the photoelectric conversion layer using the p-type molecules of Formula (1) has not only high hole mobility for crystallinity in the monolayer film but also high hole mobility for crystallinity in a photoelectric conversion layer that is a mixed layer film and, as a consequence, the capture rate of carriers from the photoelectric conversion layer to each electrode increases. In Comparative Example 1, on the other hand, the hole mobility is low in the monolayer film despite its crystallinity, and in the photoelectric conversion layer that is the mixed layer film, the hole mobility is lower than that in the monolayer film because of non-crystallinity. The capture rate of carriers hence decreases. As a consequence, the quantum efficiency and standardized response rate of Comparative Example 1 are lower than those of Example 1.

From the X-ray diffraction results illustrated in FIGS. 5 and 6, the p-type molecules of Example 1 retain high crystallinity in the photoelectric conversion layer despite their co-deposition with heteroatoms of the colorant and fullerene, presumably for the reason that, in Example 1 in which it conjugation is extended and a biphenyl structure and a ring are extended in each substituent, π-π interaction and CH-π interaction, which are intermolecular actions that form a herringbone crystal structure, are strong.

In Example 1 described above, the compound (h) in Scheme (5), out of the compounds exemplified by Formula (1), was used as p-type molecules. However, compounds represented by the following formula out of the p-type molecules exemplified by Formula (1) may each also be used.

[Chem. 28]

[Chem. 27]

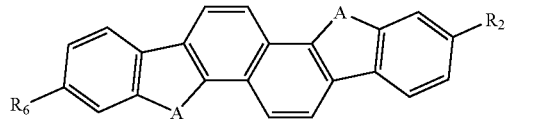

Formula (9)

The compounds exemplified by Formula (9) are different from Example 1 specifically in that instead of $R_3$ and $R_7$, $R_2$ and $R_6$ are each a substituted or unsubstituted aryl group or heteroaryl group. Among the compounds of Formula (9), compounds represented by the following formula can each also be used as p-type molecules.

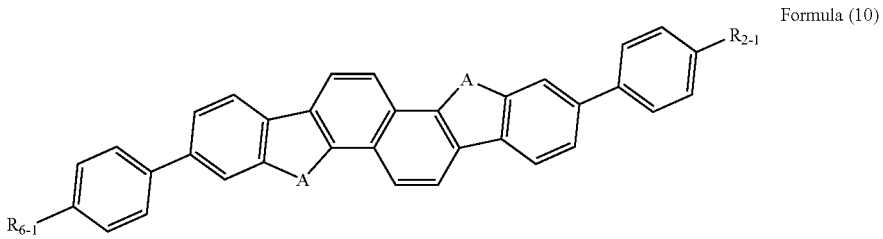

Formula (10)

in which $R_{2\text{-}1}$ and $R_{6\text{-}1}$ are each a substituted or unsubstituted aryl group or heteroaryl group having 4 to 24 carbon atoms.

Among the compounds exemplified by Formula (10), compounds represented by the following formula can each also be used as p-type molecules.

[Chem. 29]

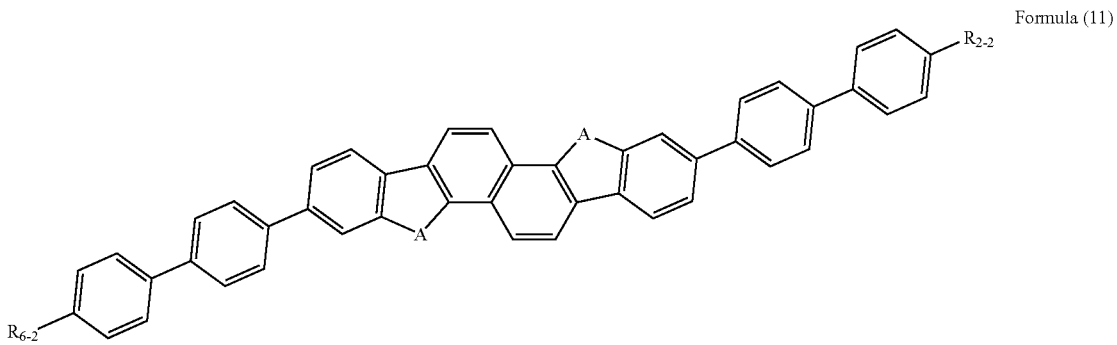

Formula (11)

in which $R_{2\text{-}2}$ and $R_{6\text{-}2}$ are each a substituted or unsubstituted aryl group or heteroaryl group having 4 to 18 carbon atoms.

Among the compounds exemplified by Formula (10), compounds represented by the following formula can each also be used as p-type molecules.

[Chem. 30]

Formula (12)

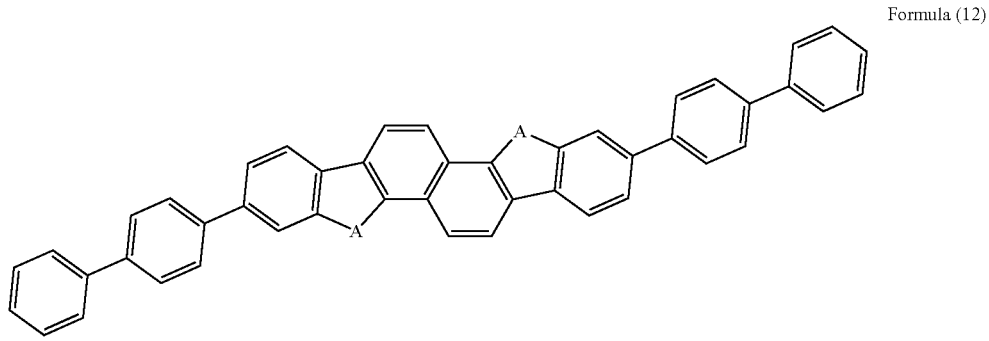

Among the compounds exemplified by Formula (12), the compound represented by the following formula can be also used as p-type molecules.

[Chem. 31]

Formula (13)

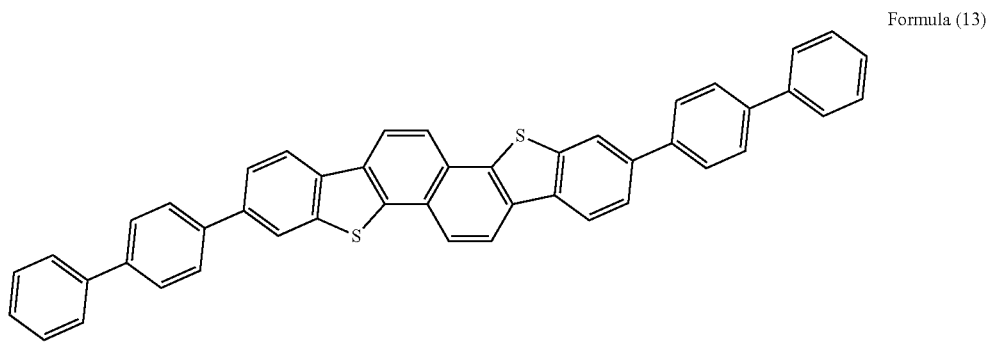

The compound represented by Formula (13) will be described in Example 2 of the first embodiment. The compound relating to Example 2 can be synthesized according to the following reaction scheme similar to Scheme (5).

Scheme (14)

[Chem. 32]

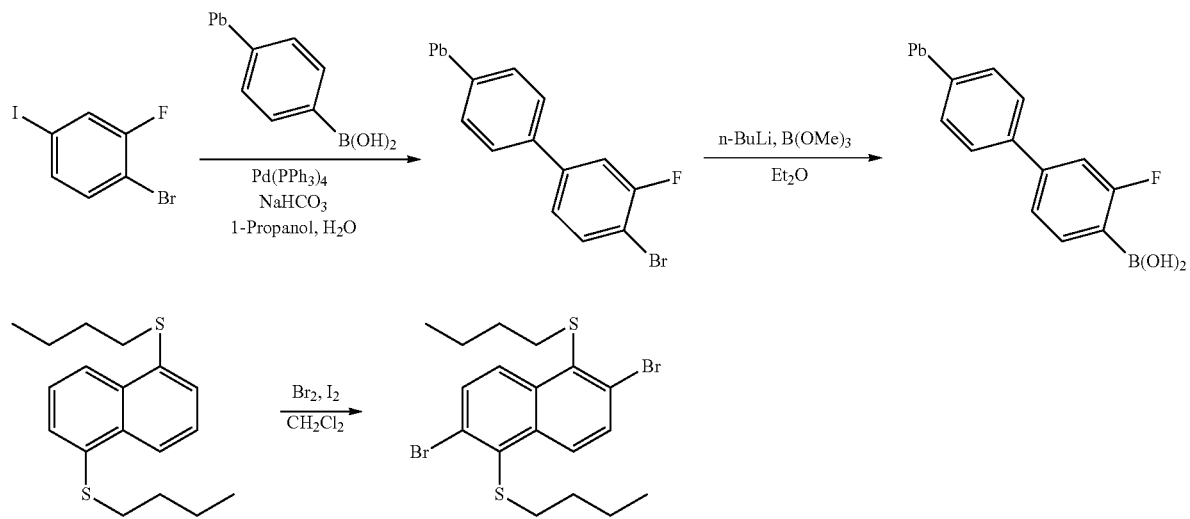

-continued

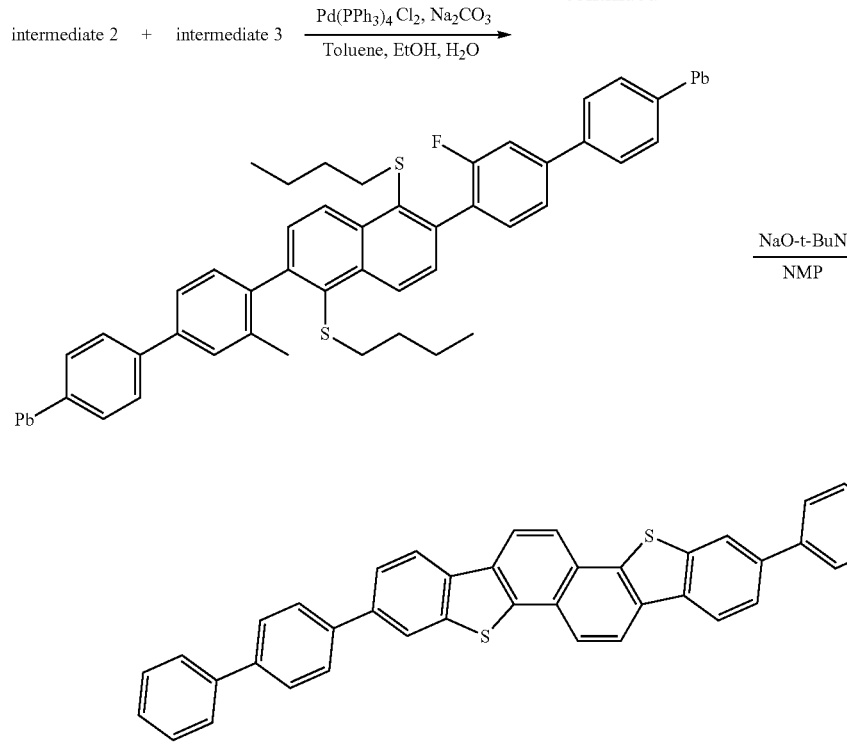

In Scheme (14), using a four-necked flask under an argon (Ar) atmosphere, 1-bromo-2-fluoro-4-iodobenzene, 4-biphenylboronic acid, sodium hydrogen carbonate and $PdCl_2(PPh_3)_2$ were first refluxed with heating in a mixed solution of distilled water and 1-propanol. Here, the chemical equivalents of 1-bromo-2-fluoro-4-iodobenzene, 4-biphenylboronic acid, sodium hydrogen carbonate and $PdCl_2(PPh_3)_2$ were "1," "1," "3" and "0.003," respectively. After allowed to cool at room temperature, the precipitated solid was collected by filtration, dissolved in dichloromethane, and collected by filtration on silica gel. As a result, a pale orange solid (the intermediate 1 of (b) in Scheme 14), was obtained with a yield of approximately 91 percent (%).

Under an argon (Ar) atmosphere, the intermediate (1) and diethyl ether were next added to a four-necked flask, followed by cooling to −72° C. over a dry ice/acetone bath. A 1.6 M solution of n-butyl lithium in hexane was next added dropwise over 40 minutes, followed by stirring for 150 minutes. Subsequently, $B(OMe)_3$ was added, and the resulting mixture was allowed to return to room temperature and was then stirred overnight. Here, the chemical equivalents of the intermediate (1), n-butyl lithium and $B(OMe)_3$ were "1," "2.5" and "3.7," respectively. Then, 2N hydrochloric acid was added to terminate the reaction, followed by filtration. As a result, a gray solid (the intermediate 2 of (c) in Scheme 14), was obtained with a yield of approximately 33 percent (%).

Under an argon (Ar) atmosphere, the raw material 3 and dichloromethane were subsequently added to a four-necked flask, followed by cooling to 0° C. Subsequently, iodine and bromine were added, and the resulting mixture was allowed to rise to room temperature, followed by stirring overnight. Here, the chemical equivalents of the raw material 3, iodine and bromine were "1," "0.03" and "2.4," respectively. Then, a 10% aqueous solution of sodium thiosulfate was added to terminate the reaction. Using chloroform, the reaction mixture was separated into layers. The organic layer was dried over anhydrous magnesium sulfate. Subsequently, the dried organic layer was filtered, and purified by column chromatography. As a result, yellow crystals (the intermediate 3 of (e) in Scheme 14), was obtained with a yield of approximately 80 percent (%).

Under an argon (Ar) atmosphere, the intermediate (2), the intermediate (3), toluene, ethanol, sodium carbonate, $PdCl_3(PPh_3)_2$ and distilled water were then added to a four-necked flask, and were refluxed with heating. Here, the chemical equivalents of the intermediate (3), the intermediate (2), sodium carbonate and $PdCl_3(PPh_3)_2$ were "1," "3," "5" and "0.009," respectively. After allowed to cool at room temperature, the precipitated solid was collected by filtration. After the solid was then dissolved in monochlorobenzene, the resulting solution was filtered using celite and silica gel. Heptane was added to the filtrate to prepare a slurry mixture, and the slurry mixture was filtered. As a result, a pale yellow solid ((f) in Scheme 14, in other words, the intermediate (4) containing impurities), was obtained with a yield of 95 percent (%).

Under an argon (Ar) atmosphere, the intermediate (4), NaO-t-Bu and NMP were subsequently added to a four-necked flask, following by stirring overnight at 160 to 170° C. The heating was then stopped, and the resulting reaction mixture was allowed to cool at room temperature. Subsequently, the reaction mixture was filtered and washed with methanol. As a result, a pale gray solid (crude product of Example 2) was obtained with a crude yield of 93 percent (%). Sublimation purification was then conducted to obtain the compound of Example 2 as exemplified by Formula (13).

Figure 7:
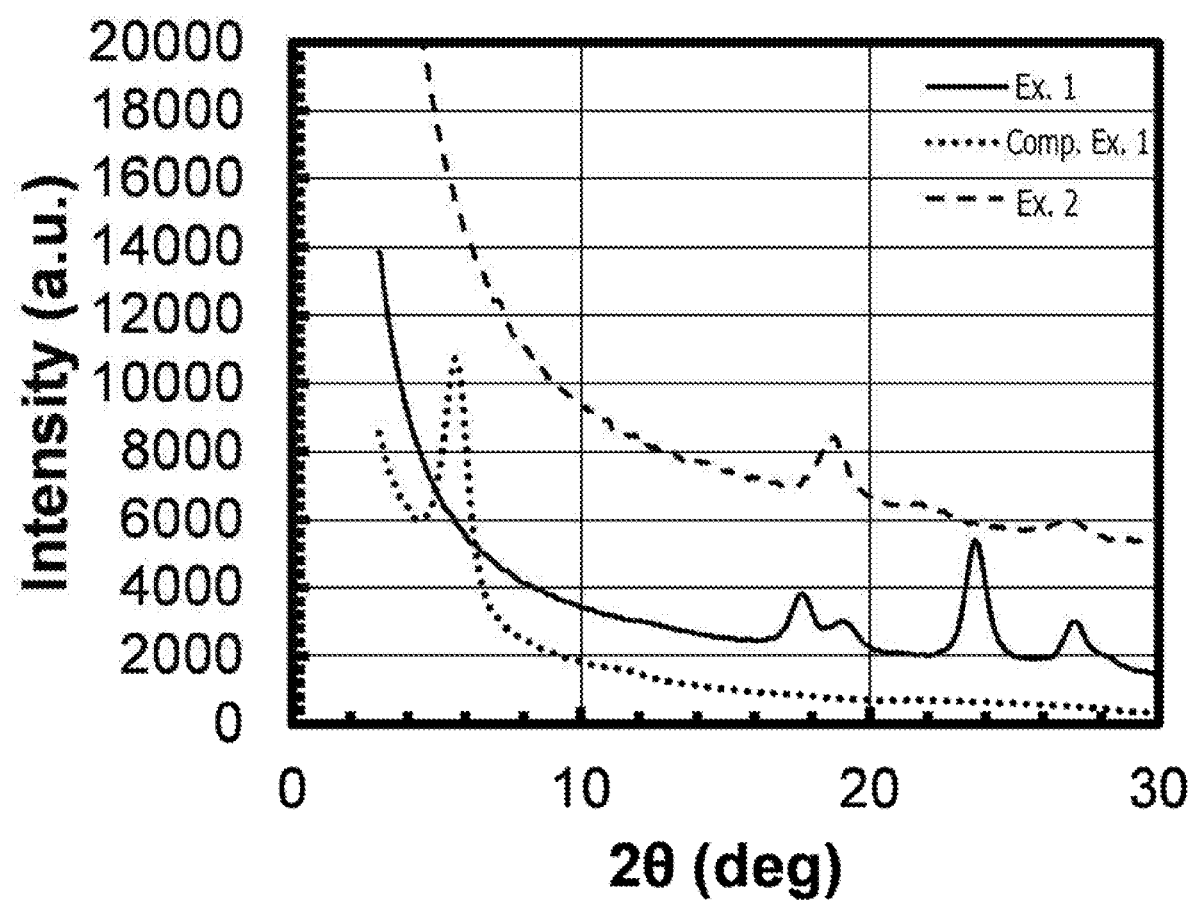
FIG. 7 is a graph illustrating an example of results of X-ray diffractometry of a monolayer film of p-type molecules in Example 2 of the first embodiment of the present technology.
Figure 8:
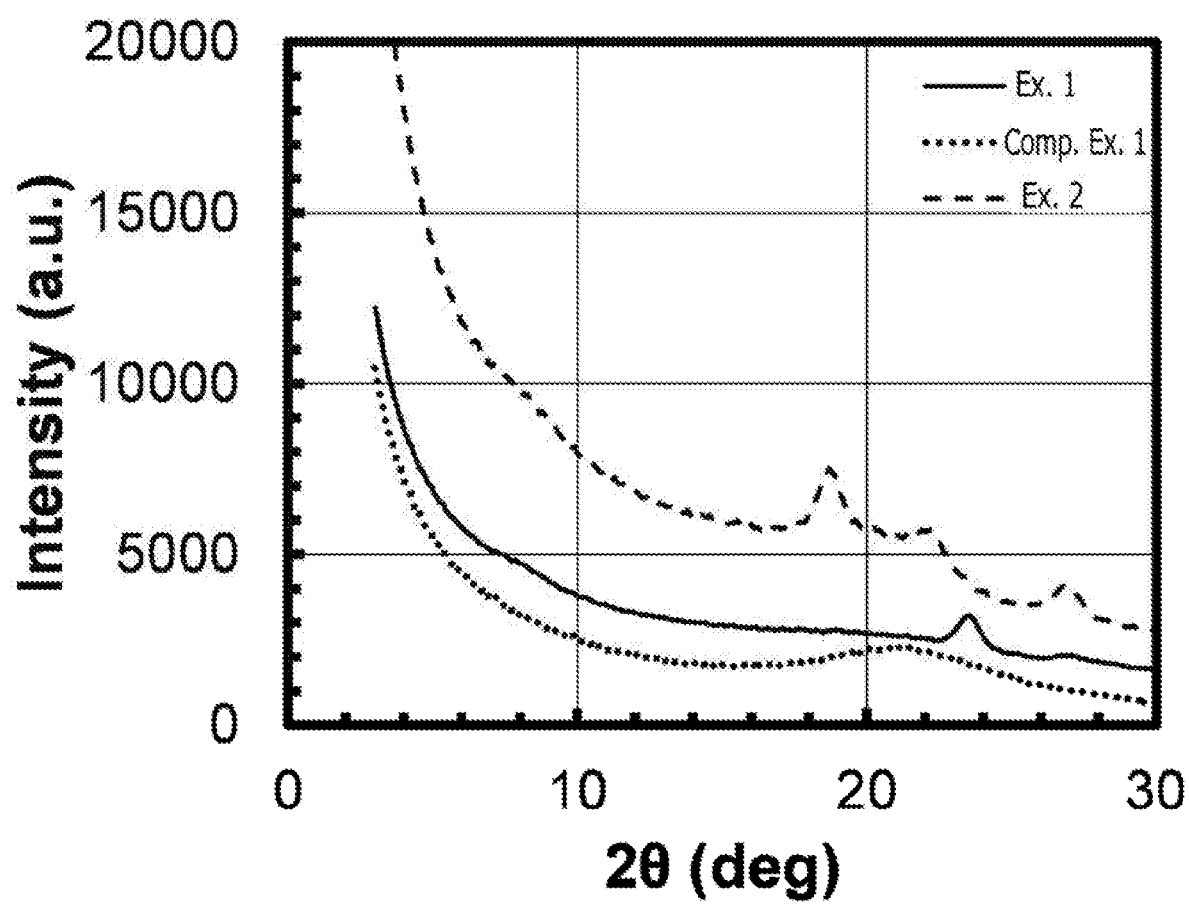
FIG. 8 is a graph illustrating an example of results of X-ray diffractometry of a photoelectric conversion layer in Example 2 of the first embodiment of the present technology.

FIGS. 7 and 8 are graphs illustrating examples of results of X-ray diffractometry in Example 2 of the first embodiment of the present technology. In these figures, the axis of ordinates represents X-ray diffraction intensity, and the axis of abscissas represents diffraction angle. FIG. 7 illustrates the results of X-ray diffractometry of monolayer films of p-type molecules, and FIG. 8 illustrates results of X-ray diffractometry of photoelectric conversion layers. Solid-line loci represent the diffraction results of Example 1, fine-dotted-line loci represent the diffraction results of Comparative Example 1, and coarse-dotted-line loci represent the diffraction results of Example 2.

The evaluation results of the individual characteristics of Example 1, Example 2 and Comparative Example 1 are presented in the following table. Further, these device structures are all bulk-heterostructures.

TABLE 2

|  | First embodiment: Ex. 1 | First embodiment: Ex. 2 | Comp. Ex. 1 |
|---|---|---|---|
| p-Type molecules | Compound (h) in Scheme (5) | Compound (g) in Scheme (14) | Formula (8) |
| External quantum efficiency (%) | 80 | 94 | 77 |
| Dark current (A/cm$^2$) | 1.0E−10 | 1.0E−10 | 3.0E−10 |
| Standardized response rate (a.u.) | 1 | 0.4 | 10 |
| Hole mobility through monolayer (cm$^2$/V · s) | 1.4E−06 | 2.7E−06 | 8.1E−08 |
| Monolayer crystallinity | Present | Present | Present |
| Hole mobility through photoelectric conversion layer (cm$^2$/V · s) | 1.9E−05 | 5.1E−05 | 1.5E−09 |
| Crystallinity of photoelectric conversion layer | Present | Present | Absent |

From a comparison between Example 2 and Comparative Example 1, it is appreciated that in Example 2, the crystallinity in the monolayer is retained even in the photoelectric conversion layer (bulk-heterostructure). This phenomenon is similar in tendency to the results of the compound (h) (Example 1) in Scheme 5. The comparison between Example 2 and Comparative Example 1 also indicates that Example 2, in which the photoelectric conversion layer has a high crystallinity, is superior in external quantity efficiency and response characteristics and that the retention of crystallinity in a photoelectric conversion layer is important for improved element characteristics. Therefore, it is essential for improved element characteristics to conduct molecular design so that the interaction between p-type molecules becomes greater, and as the positions of substituents in Formula (1), the combination of $R_3$ and $R_7$ is preferred with the combination of $R_2$ and $R_6$ being more preferred. In a case of being named according to the IUPAC (International Union of Pure and Applied Chemistry), the positions of substitution on the mother skeleton are preferably the 2- and 9-positions, more preferably the 3- and 10-positions.

It is to be noted that among the compounds exemplified by Formula (1), compounds represented by the following formulas can be used.

[Chem. 33]

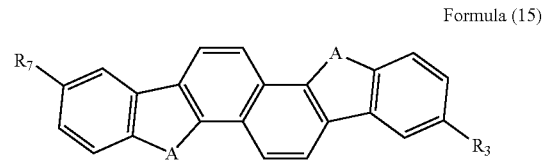

Formula (15)

The above-described compound of Example 1 is one of the compounds exemplified by Formula (15). Among the compounds of Formula (15), compounds represented by the following formula can each also be used as p-type molecules in addition to the compound of Example 1.

[Chem. 34]

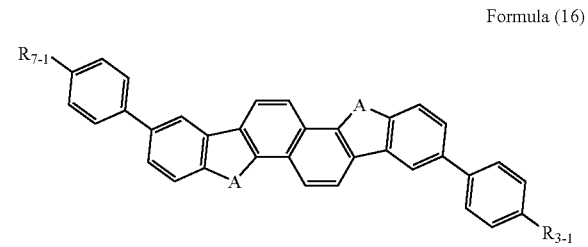

Formula (16)

in which $R_{3-1}$ and $R_{7-1}$ are each a substituted or unsubstituted aryl group or heteroaryl group having 4 to 24 carbon atoms.

Among the compounds exemplified by Formula (16), the compounds represented by the following formula can each be used.

[Chem. 35]

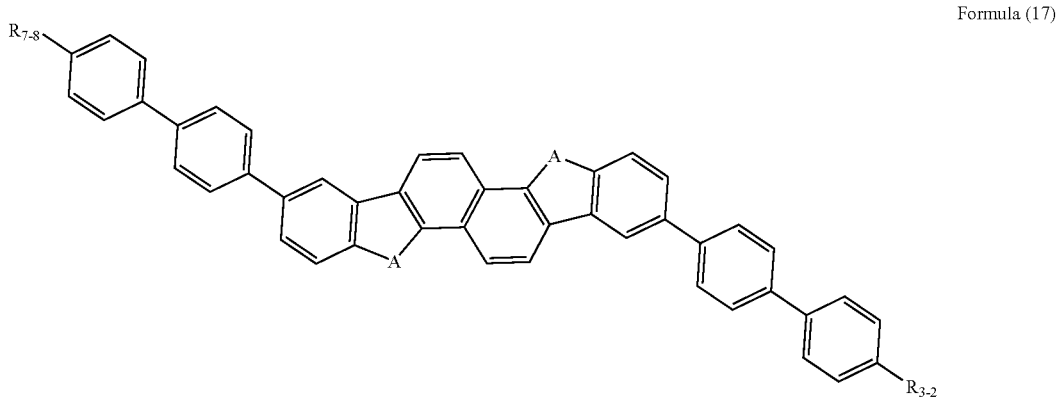

Formula (17)

in which $R_{3-2}$ and $R_{7-2}$ are each a substituted or unsubstituted aryl group or heteroaryl group having 4 to 18 carbon atoms.

Among the compounds exemplified by Formula (16), compounds represented by the following formula can each also be used in addition to the compounds of Formula (17).

[Chem. 36]

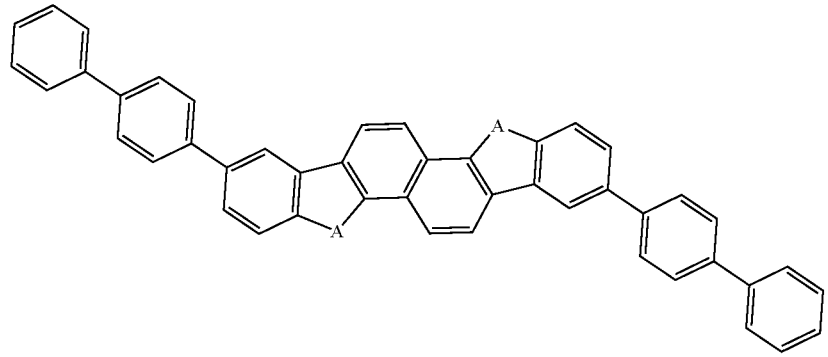

Among the compounds exemplified by Formula (18), the compound represented by the following formula can be used.

[Chem. 37]

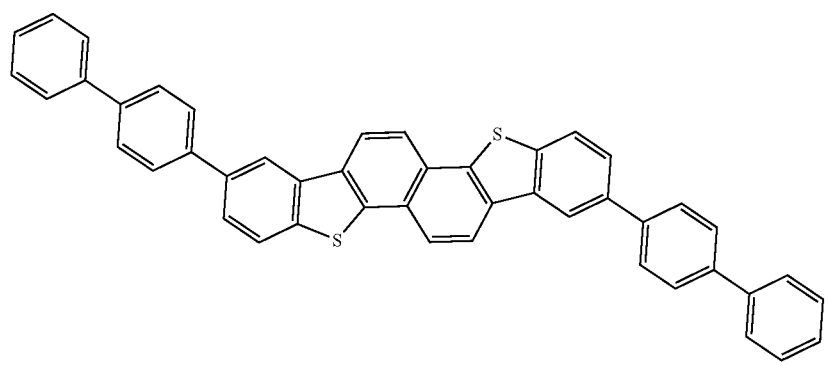

As described above, according to the first embodiment of the present technology, the organic photoelectric conversion element 240 can be provided with improved quantum efficiency and standardized response rate owing to the formation of the photoelectric conversion layer 243 including the p-type molecules represented by Formula (1).

2. Second Embodiment

In the first embodiment described above, the quantum efficiency and response rate were improved using, as p-type molecules, the compounds represented by Formula (1). However, it is also possible to make improvements in quantum efficiency and response rate by using, as p-type molecules, compounds other than those of Formula (1). An organic photoelectric conversion element 240 in this second embodiment is different from that in the first embodiment in that a compound other than those of Formula (1) are included.

The organic photoelectric conversion element 240 in the second embodiment is different from that in the first embodiment in that a photoelectric conversion layer 243 includes p-type molecules represented by Formula (9) instead of the p-type molecules represented by Formula (1).

Formula (18)

Formula (19)

[Chem. 38]

Formula (20)

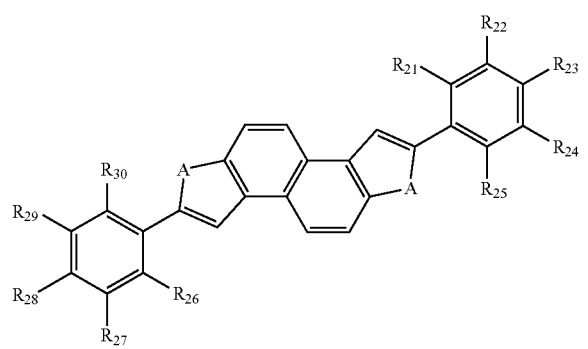

in which A represents any one of oxygen, sulfur or selenium, any one of $R_{21}$ to $R_{25}$ represents a substituted or unsubstituted aryl or heteroaryl having 4 to 30 carbon atoms, the remainder of $R_{21}$ to $R_{25}$ each represent hydrogen, any one of $R_{26}$ to $R_{30}$ represents a substituted or unsubstituted aryl or heteroaryl having 4 to 30 carbon atoms, and the remainder of $R_{26}$ to $R_{30}$ each represent hydrogen.

As the positions of substitution by aryl groups or heteroaryl groups in Formula (20), the combination of $R_{23}$ and $R_{28}$ is most desired for the reason that a linear, fused-ring molecule of high planarity like Formula (9) is known to have a herringbone crystal structure and to form a two-dimensional carrier transport path and the molecular shape is desirably linear in order to have such a crystal structure. The selection of aryl groups or heteroaryl groups as $R_{23}$ and $R_{28}$ allows the positions of substitution to be linear.

For a similar reason, even if each aryl group is not single but is connected to a biphenyl group or a terphenyl group, each ring of the aryl group is desirably connected at the para position thereof to the biphenyl or terphenyl group from the viewpoint of providing linearity. If a five-membered ring such as a bithienyl group or terthienyl group is connected to an aryl group, the connection via the carbon at the alpha position of the thiophene ring is desired for higher linearity. Further, if a phenyl group and a thienyl group are connected to each other, the connection between the para-position of the phenyl group and the alpha position of the thienyl group is desired for a similar reason. In addition, if each aryl group or each heteroaryl group includes a fused multi-ring group such as naphthalene ring, benzothiophene ring or indole ring, they are desirably also connected to provide high linearity.

The substituents of $R_{21}$ to $R_{25}$ and of $R_{26}$ to $R_{30}$ are desirably the same, and in addition the symmetry of the positions of substitution is desirably twofold symmetry, for the reason that, when having a crystal structure, higher symmetry leads to smaller anisotropy and to a smaller band dispersion width.

Example 1

A description will next be made about Example 1 in the second embodiment. In Example 1, p-type molecules were synthesized according to the following reaction scheme with reference to Scheme (2) in Shoji Shinamura, et. al., "Linear- and Angular-Shaped Naphthodithiophenes: Selective Synthesis, Properties, and Application to Organic Field-Effect Transistors," J. Am. Chem. Soc., 2011, 133, 5024-5035, and sublimation purification was conducted for the resulting reaction product.

Scheme (21)

[Chem. 39]

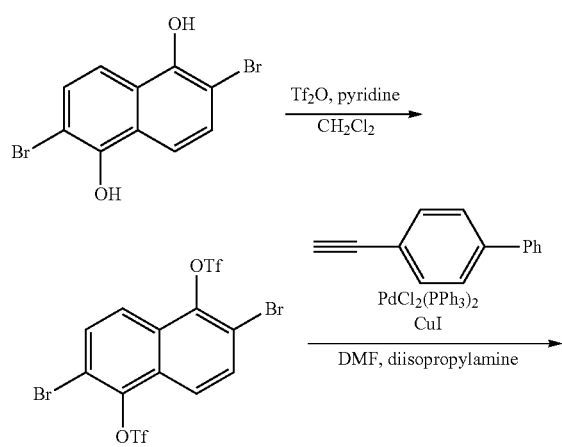

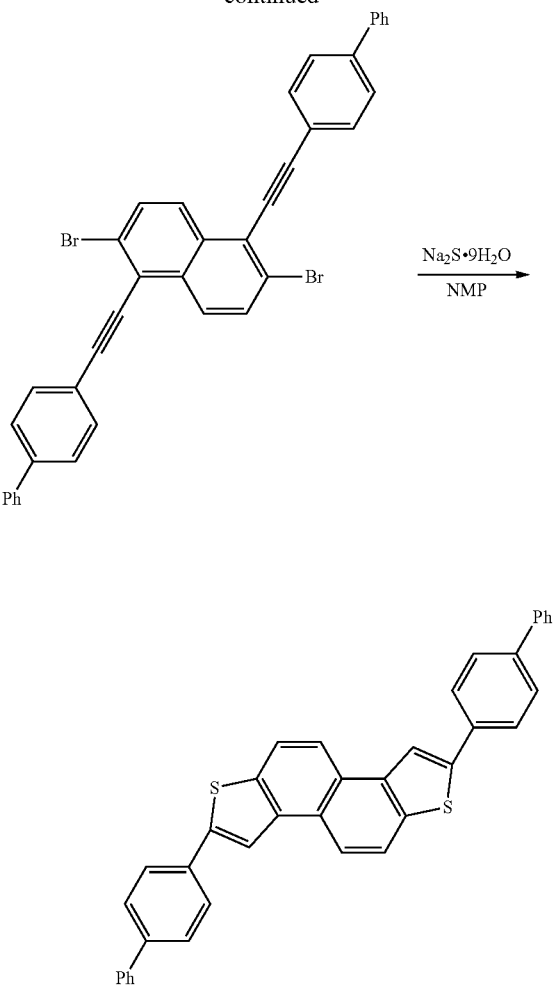

The compound (d) in Scheme (21) is an example of the compounds of Formula (20). In Example 1, the preparation processes of the parts other than p-type molecules were similar those in Example 1.

Comparative Example 1

A description will next be made about Comparative Example 1. p-Type molecules according to Comparative Example 1 were synthesized according to the following reaction scheme with reference to Scheme (2) in Shoji Shinamura, et. al., "Linear- and Angular-Shaped Naphthodithiophenes: Selective Synthesis, Properties, and Application to Organic Field-Effect Transistors," J. Am. Chem. Soc., 2011, 133, 5024-5035, and sublimation purification was conducted for the resulting reaction product. Compared with the compound (d) in Scheme (21) in Example 1, the compound (d) in Scheme (22) lacks of one phenyl group in each of the substituents at the opposite terminals.

[Chem. 40]

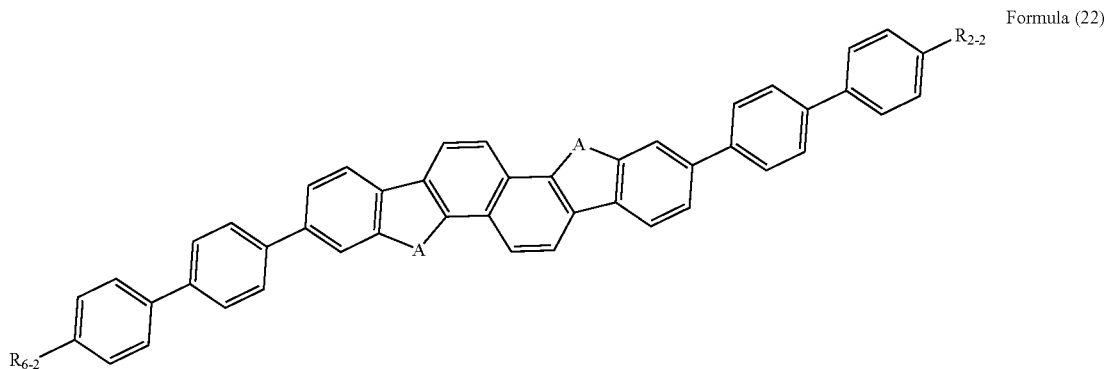

Formula (22)

Comparative Example 2

A description will next be made about a comparative example in the first embodiment. In Comparative Example 2, BQD represented by Formula (8) of a quinacridone derivative was used as p-type molecules.

[Characteristics of Photoelectric Conversion Elements]

Evaluation methods of characteristics of an organic photoelectric conversion element according to Example 1 and organic photoelectric conversion elements according to Comparative Examples 1 and 2 were similar to those in the first embodiment.

Figure 9:
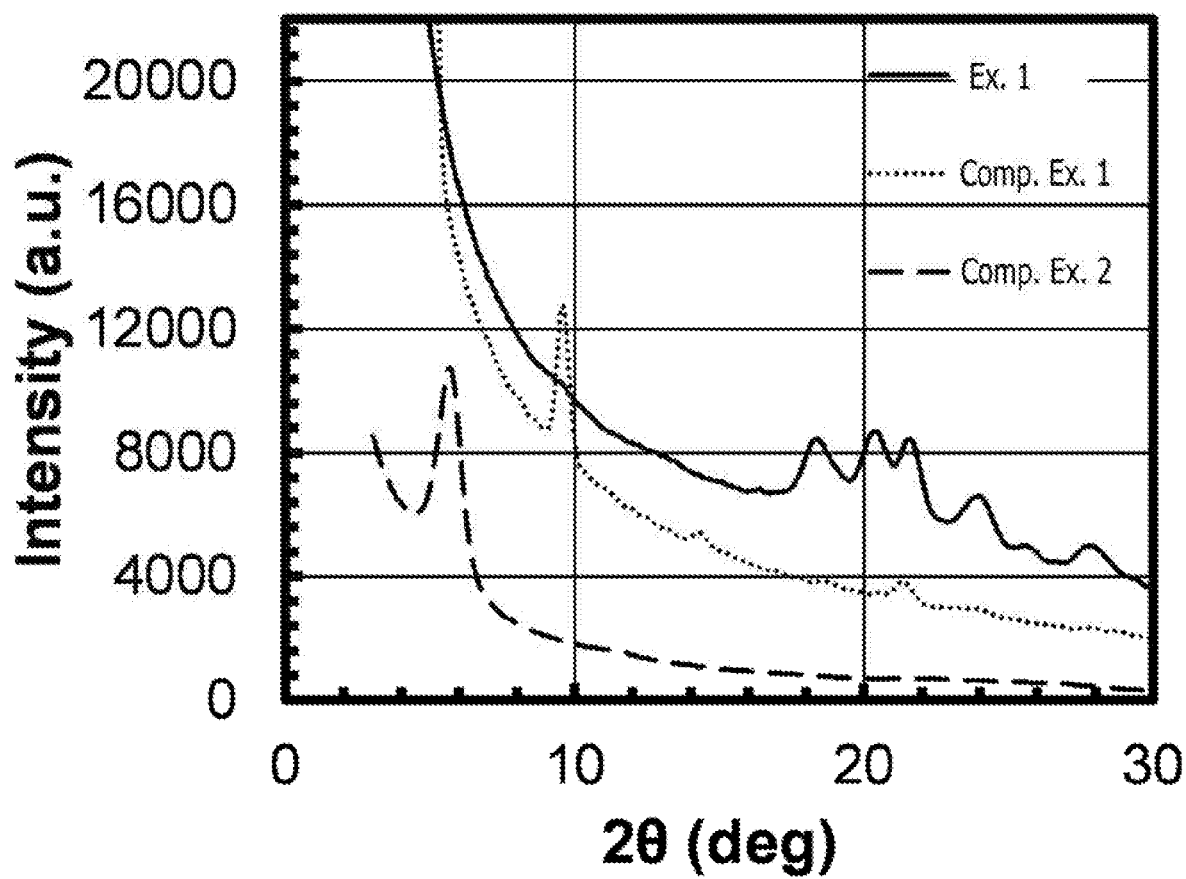
FIG. 9 is a graph illustrating an example of X-ray diffraction results of a monolayer film of p-type molecules in a second embodiment of the present technology.
Figure 10:
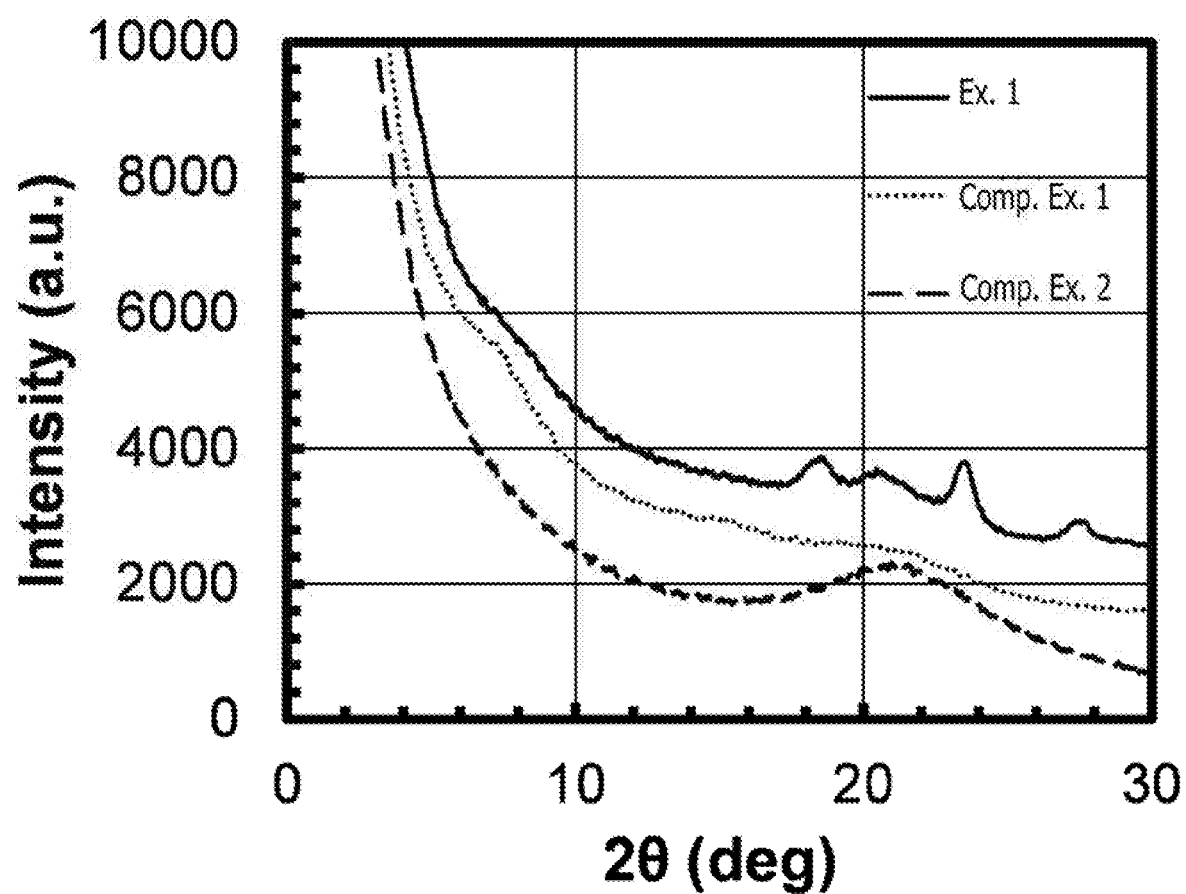
FIG. 10 is a graph illustrating an example of results of X-ray diffractometry of a photoelectric conversion layer in the second embodiment of the present technology.

FIGS. 9 and 10 are graphs illustrating examples of results of X-ray diffractometry in the second embodiment of the present technology. In these figures, the axis of ordinates represents X-ray diffraction intensity, and the axis of abscissas represents diffraction angle. FIG. 9 illustrates the results of X-ray diffractometry of monolayer films of p-type molecules, and FIG. 10 illustrates results of X-ray diffractometry of photoelectric conversion layers. Solid-line loci represent the diffraction results of Example 1, dotted-line loci represent the diffraction results of Comparative Example 1, and dashed-line loci represent the diffraction results of Comparative Example 2. As exemplified in FIG. 9, the p-type molecular monolayer films used in Example 1, Comparative Example 1 and Comparative Example 2 in the second embodiment each produced one or more peaks in X-ray diffraction intensity, and were each crystalline. As exemplified in FIG. 10, on the other hand, peaks were produced in X-ray diffraction intensity from the photoelectric conversion layer of Example 1 in the second embodiment, but no peak was produced from the photoelectric conversion layers of Comparative Examples 1 and 2. It is therefore possible to determine that crystallinity is present in the photoelectric conversion layer of Example 1 while crystallinity is absent in the photoelectric conversion layers of Comparative Examples 1 and 2. Here, in the determination of the presence or absence of crystallinity, crystallinity was determined to be present if there was a peak having a peak intensity higher by 5 times or greater than the noise level of the base line and a shape with a half-width value of smaller than 1°.

The evaluation results of the individual characteristics in Example 1 and comparative examples are presented in the following table.

TABLE 3

| | Second embodiment: Ex. 1 | Comp. Ex. 1 | Comp. Ex. 2 |
|---|---|---|---|
| p-Type molecules | Compound (d) in Formula (10) | Compound (d) of Formula (11) | Formula (8) |
| External quantum efficiency (%) | 81 | 22 | 77 |
| Dark current (A/cm$^2$) | 2.0E−10 | 8.0E−10 | 3.0E−10 |
| Standardized response rate (a.u.) | 2 | >300 | 10 |
| Hole mobility through monolayer (cm$^2$/V · s) | 3.1E−05 | 3.9E−04 | 8.1E−08 |
| Monolayer crystallinity | Present | Present | Present |
| Hole mobility through photoelectric conversion layer (cm$^2$/V · s) | 7.1E−05 | 2.0E−08 | 1.5E−09 |
| Crystallinity of photoelectric conversion layer | Present | Absent | Absent |

The external quantum efficiency, dark current and standardized response rate of the photoelectric conversion element in Example 1 were 81 percent (%), 2.0E-10 ampere per square centimeter (A/cm$^2$) and 2. The monolayer of the p-type molecules used in Example 1 had crystallinity, and its SCLC (Space-Charge-Limited Current) mobility (in other words, hole mobility) was 3.1E-5 square centimeter per volt-second (cm$^2$N s). The photoelectric conversion layer in the photoelectric conversion element in Example 1 had crystallinity, and the SCLC mobility (hole mobility) of the photoelectric conversion layer was 7.1E-5 square centimeter per volt-second (cm$^2$/V·s).

The external quantum efficiency, dark current and standardized response rate of the photoelectric conversion element in Comparative Example 1 were 22 percent (%), 8.0E-10 ampere per square centimeter (A/cm$^2$) and >300. The monolayer of the p-type molecules used in Comparative Example 1 had crystallinity, and its SCLC mobility (hole mobility) was 3.9E-4 square centimeter per volt-second (cm$^2$/V·s). The photoelectric conversion layer in the photoelectric conversion element of the comparative example had non-crystallinity, and the SCLC mobility (hole mobility) of the photoelectric conversion layer was 2.0E-8 square centimeter per volt-second (cm$^2$/V·s). On the other hand, the characteristics of the photoelectric conversion element in Comparative Example 2 were as described above.

As appreciated from the foregoing, the quantum efficiency and standardized response rate of the organic photoelectric conversion element in Example 1 are higher than those of Comparative Examples 1 and 2. This is presumably attributable to the fact that the photoelectric conversion layer using the p-type molecules of Formula (20) has high hole mobility for its crystallinity and, as a consequence, the capture rate of carriers from the photoelectric conversion layer to each electrode increases. In each of Comparative Examples 1 and 2, on the other hand, the photoelectric conversion layer is non-crystalline so that the hole mobility is low and the capture rate of carriers is low. As a consequence, the quantum efficiency and standardized response rate of each comparative example are lower than those of Example 1.

From X-ray diffraction results, the p-type molecules of Example 1 retain high crystallinity in the photoelectric conversion layer despite their co-deposition with heteroatoms of the colorant and fullerene, presumably for the reason that the biphenyl-substituted derivative of Example 1 has stronger CH-π interaction, which is intermolecular action that forms a herringbone crystal structure, than the monophenyl-substituted derivative of Comparative Example 1.

From a comparison with BQD of Comparative Example 2, the higher quantum efficiency of the biphenyl-substituted derivative of Example 1 than the phenyl-substituted derivative of Comparative Example 1 can also be attributed to the fact that the domain size had enlarged for not only the crystallinity of the photoelectric conversion layer but also promoted phase separation in the photoelectric conversion layer. An increase in domain size is considered to lead to the diffusion of excitons, which are formed in the colorant, to an interface so that the excitons are deactivated before separation into charges. In the photoelectric conversion layer according to the present technology, the biphenyl-substituted derivative presumably has, compared to the phenyl-substituted derivative, intermolecular interaction such that upon formation of a film by vapor deposition, the phase separation size between the colorant and the n-type molecules becomes an appropriate size not greater than an excitation diffusion length.

According to the second embodiment of the present technology as described above, the photoelectric conversion layer 243 was formed, with p-type molecules of Formula (9) included therein, in the organic photoelectric conversion element 240 so that the organic photoelectric conversion element 240 was successfully provided with the improved quantum efficiency and response rate.

It is to be noted that the above-described embodiments merely present examples for embodying the present technology, and the matters in the embodiments and the invention-specifying features in the claims have corresponding relationships, respectively. Similarly, the invention-specifying features in the claims and the matters identified in the same terms in the embodiments of the present technology have corresponding relationships, respectively. However, the present technology should not be limited to the embodiments, but can be embodied by applying various modifications to the embodiments within a scope not departing from its spirit.

It is also to be noted that the advantageous effects described in the Description are merely illustrative and are not limiting, and there may be other advantageous effects.

It is also to be noted that the present technology may have configurations as will be described hereinafter.

(1) An organic photoelectric conversion element including:

p-type molecules represented by Formula (1) in a photoelectric conversion layer:

[Chem. 41]

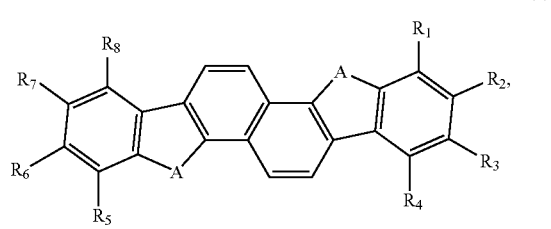

Formula (1)

in which in the Formula (1), A represents any one of oxygen, sulfur or selenium, any one of $R_1$ to $R_4$ represents a substituted or unsubstituted aryl or heteroaryl having 4 to 30 carbon atoms, the remainder of $R_1$ to $R_4$ each represent hydrogen, any one of $R_5$ to $R_8$ represents a substituted or unsubstituted aryl or heteroaryl having 4 to 30 carbon atoms, and the remainder of $R_5$ to $R_8$ each represent hydrogen.

(2) The organic photoelectric conversion element as described above in (1), in which the photoelectric conversion layer further includes n-type molecules, and the n-type molecules include a fullerene or a fullerene derivative.

(3) The organic photoelectric conversion element as described above in (2), in which the n-type molecules amount to a volume fraction of 10 to 50 percent relative to the photoelectric conversion layer.

(4) The organic photoelectric conversion element as described above in (2) or (3), in which the n-type molecules include the fullerene derivative represented by any one of Formula (2) or (3):

[Chem. 42]

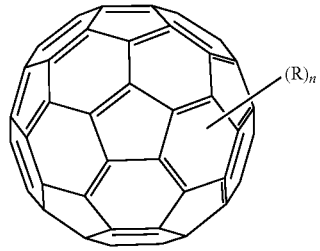

Formula (2)

[Chem. 43]

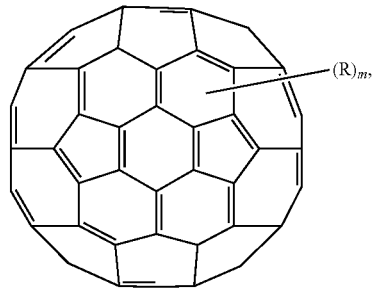

Formula (3)

in the Formulae (2) and (3), R independently represents hydrogen, halogen, linear, branched or cyclic alkyl, phenyl, a linear or fused-ring aromatic-containing group, a halogenide-containing group, partial fluoroalkyl, perfluoroalkyl, silylalkyl, silylalkoxy, arylsilyl, arylsulfanyl, alkylsulfanyl, arylsulfonyl, alkylsulfonyl, arylsulfido, alkylsulfido, amino, alkylamino, arylamino, hydroxy, alkoxy, acylamino, acyloxy, carbonyl, carboxy, carboxamido, carboalkoxy, acyl, sulfonyl, cyano, nitro, a chalcogenide-containing group, phosphino or phosphono, or a derivative thereof, and n and m each stand for an integer.

(5) The organic photoelectric conversion element as described above in any one of (1) to (4), in which
the photoelectric conversion layer further includes a colorant, and
the colorant has a maximum absorption coefficient of not smaller than 50000 cm$^{-1}$ in a wavelength range of visible light.

(6) The organic photoelectric conversion element as described above in (5), in which
the colorant amounts to a volume fraction of 20 to 80 percent relative to the photoelectric conversion layer.

(7) The organic photoelectric conversion element as described above in (5) or (6), in which
the colorant includes a subphthalocyanine derivative.

(8) The organic photoelectric conversion element as described above in (7), in which
the colorant includes a subphthalocyanine derivative represented by Formula (4):

[Chem. 44]

Formula (4)

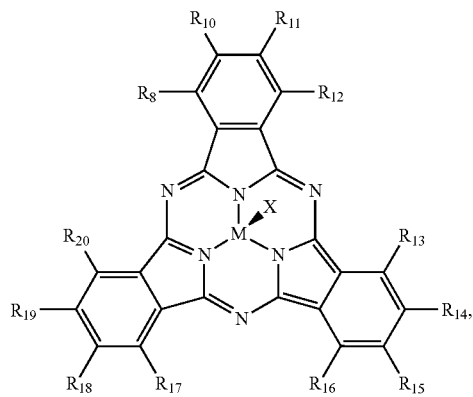

and
$R_9$ to $R_{20}$ in the Formula (4) are each independently selected from a group including hydrogen, halogen, linear, branched or cyclic alkyl, thioalkyl, thioaryl, arylsulfonyl, alkylsulfonyl, amino, alkylamino, arylamino, hydroxy, alkoxy, acylamino, acyloxy, phenyl, carboxy, carboxamido, carboalkoxy, acyl, sulfonyl, cyano and nitro, M represents boron or a divalent or trivalent metal, and X represents an anionic group.

(9) The organic photoelectric conversion element as described above in any one of (1) to (8), in which
the p-type molecules amount to a volume fraction of 10 to 70 percent relative to the photoelectric conversion layer.

(10) The organic photoelectric conversion element as described above in any one of (1) to (9), in which
the photoelectric conversion layer includes, as the p-type molecules, a compound represented by Formula (9) out of the compounds represented by Formula (1):

[Chem. 45]

Formula (9)

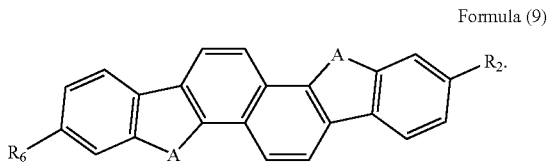

(11) The organic photoelectric conversion element as described above in (10), in which
the photoelectric conversion layer includes, as the p-type molecules, a compound represented by Formula (10) out of the compounds represented by Formula (9):

[Chem. 46]

Formula (10)

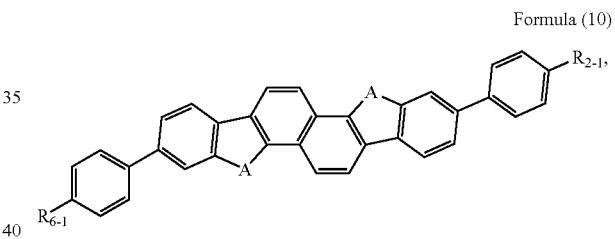

and
$R_{2-1}$ and $R_{6-1}$ are each a substituted or unsubstituted aryl group or heteroaryl group having 4 to 24 carbon atoms.

(12) The organic photoelectric conversion element as described above in (11), in which
the photoelectric conversion layer includes, as the p-type molecules, a compound represented by Formula (11) out of the compounds represented by Formula (10):

[Chem. 47]

Formula (11)

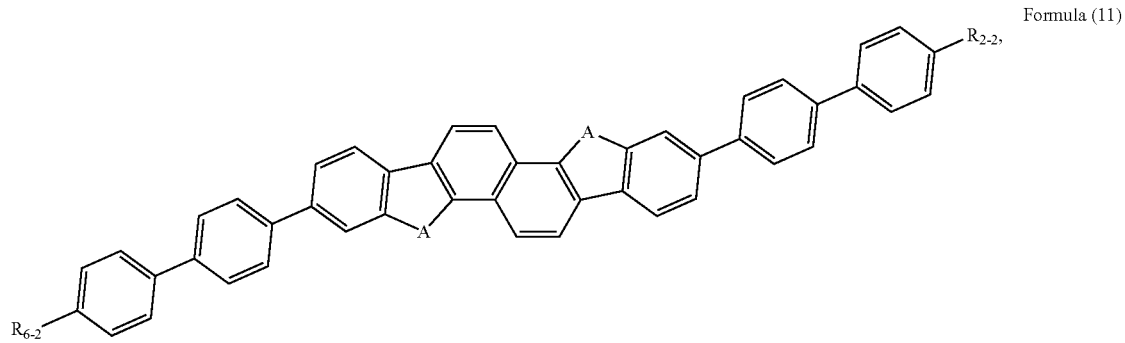

and in the Formula (11), $R_{2\text{-}2}$ and $R_{6\text{-}2}$ are each a substituted or unsubstituted aryl group or heteroaryl group having 4 to 18 carbon atoms.

(13) The organic photoelectric conversion element as described above in (11), in which the photoelectric conversion layer includes, as the p-type molecules, a compound represented by Formula (12) out of the compounds represented by Formula (10):

[Chem. 48]

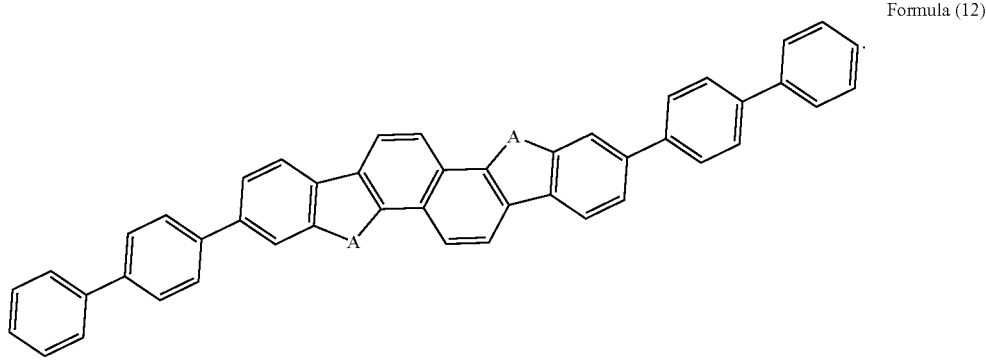

Formula (12)

(14) The organic photoelectric conversion element as described above in (13), in which the photoelectric conversion layer includes, as the p-type molecules, a compound represented by Formula (13) out of the compounds represented by Formula (12):

[Chem. 49]

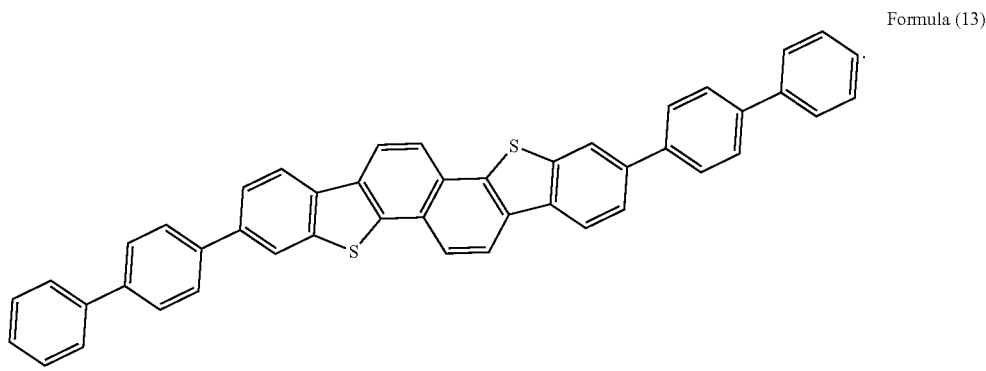

Formula (13)

(15) The organic photoelectric conversion element as described above in any one of (1) to (9), in which the photoelectric conversion layer includes, as the p-type molecules, a compound represented by Formula (15) out of the compounds represented by Formula (1):

[Chem. 50]

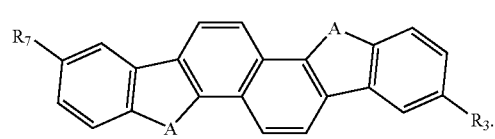

Formula (15)

(16) The organic photoelectric conversion element as described above in (15), in which the photoelectric conversion layer includes, as the p-type molecules, a compound represented by Formula (16) out of the compounds represented by Formula (15):

[Chem. 51]

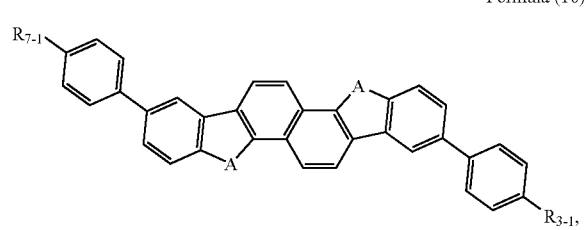

Formula (16)

and in the Formula (16), $R_{3\text{-}1}$ and $R_{7\text{-}1}$ are each a substituted or unsubstituted aryl group or heteroaryl group having 4 to 24 carbon atoms.

(17) The organic photoelectric conversion element as described above in (16), in which the photoelectric conversion layer includes, as the p-type molecules, a compound represented by Formula (17) out of the compounds represented by Formula (16):

[Chem. 52]

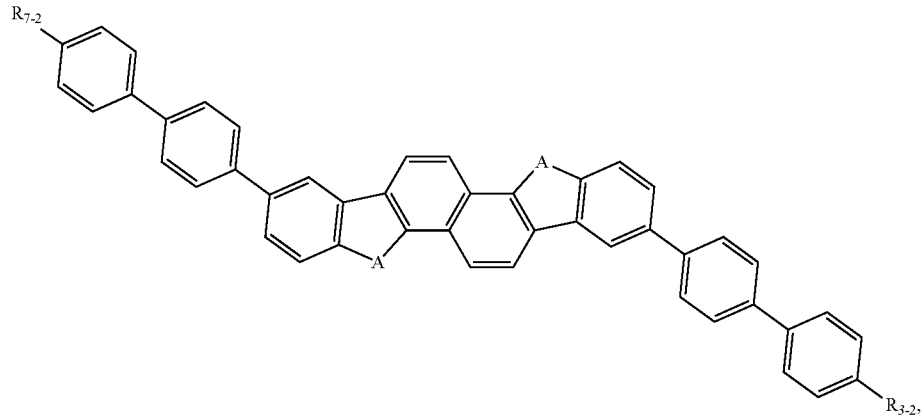

Formula (17)

and in the Formula (17), $R_{3-2}$ and $R_{7-2}$ are each a substituted or unsubstituted aryl group or heteroaryl group having 4 to 18 carbon atoms.

(18) The organic photoelectric conversion element as described above in (16), in which the photoelectric conversion layer includes, as the p-type molecules, a compound represented by Formula (18) out of the compounds represented by Formula (16):

[Chem. 53]

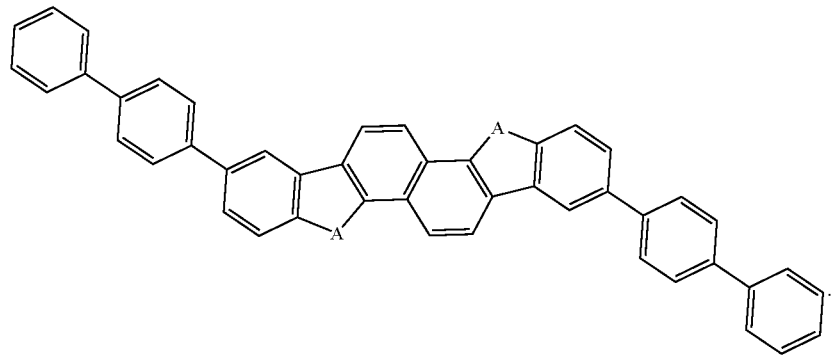

Formula (18)

(19) The organic photoelectric conversion element as described above in (18), in which the photoelectric conversion layer includes, as the p-type molecules, a compound represented by Formula (19) out of the compounds represented by Formula (18):

[Chem. 54]

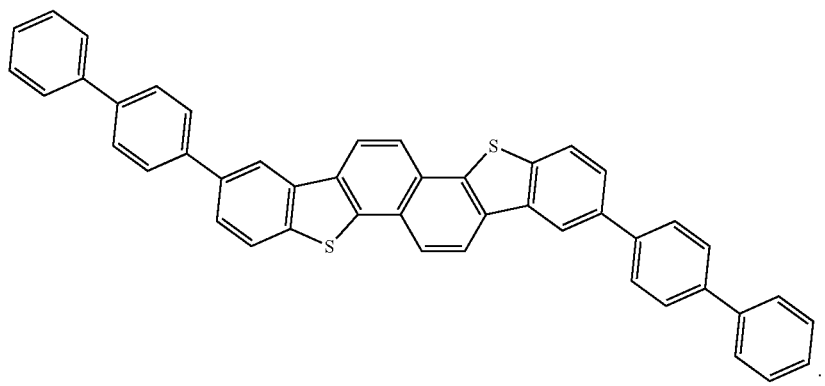

Formula (19)

(20) An organic photoelectric conversion element including:

p-type molecules represented by Formula (20) in a photoelectric conversion layer:

[Chem. 55]

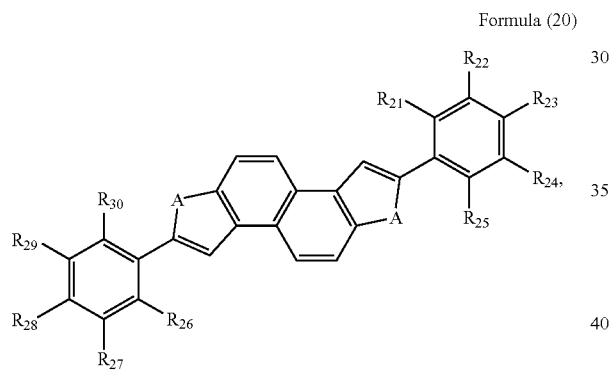

Formula (20)

in which in the Formula (20), A represents any one of oxygen, sulfur or selenium, any one of $R_{21}$ to $R_{25}$ represents a substituted or unsubstituted aryl or heteroaryl having 4 to 30 carbon atoms, the remainder of $R_{21}$ to $R_{25}$ represent hydrogen, any one of $R_{26}$ to $R_{30}$ represents a substituted or unsubstituted aryl or heteroaryl having 4 to 30 carbon atoms, and the remainder of $R_{26}$ to $R_{30}$ represent hydrogen.

(21) The organic photoelectric conversion element as described above in (20), in which the photoelectric conversion layer further includes n-type molecules, and the n-type molecules include a fullerene or a fullerene derivative.

(22) The organic photoelectric conversion element as described above in (21), in which the n-type molecules amount to a volume fraction of 10 to 50 percent relative to the photoelectric conversion layer.

(23) The organic photoelectric conversion element as described above in (21) or (22), in which the n-type molecules include the fullerene derivative represented by any one of Formula (2) or (3):

[Chem. 56]

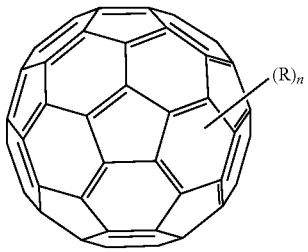

Formula (2)

[Chem. 57]

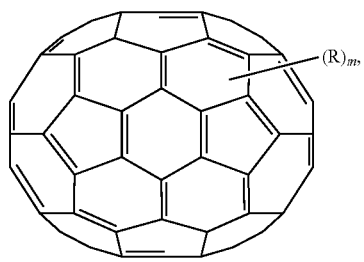

Formula (3)

and in the Formulae (2) and (3), R independently represents hydrogen, halogen, linear, branched or cyclic alkyl, phenyl, a linear or fused-ring aromatic-containing group, a halogenide-containing group, partial fluoroalkyl, perfluoroalkyl, silylalkyl, silylalkoxy, arylsilyl, arylsulfanyl, alkylsulfanyl, arylsulfonyl, alkylsulfonyl, arylsulfido, alkylsulfido, amino, alkylamino, arylamino, hydroxy, alkoxy, acylamino, acyloxy, carbonyl, carboxy, carboxamido, carboalkoxy, acyl, sulfonyl, cyano, nitro, a chalcogenide-containing group, phosphino or phosphono, or a derivative thereof, and n and m each stand for an integer.

(24) The organic photoelectric conversion element as described above in (20), in which the photoelectric conversion layer further includes a colorant, and the colorant has a maximum absorption coefficient of not smaller than 50000 $cm^{-1}$ in a wavelength range of visible light.

(25) The organic photoelectric conversion element as described above in (24), in which
the colorant amounts to a volume fraction of 20 to 80 percent relative to the photoelectric conversion layer.
(26) The organic photoelectric conversion element as described above in (24) or (25), in which
the colorant includes a subphthalocyanine derivative.
(27) The organic photoelectric conversion element as described above in (26), in which
the colorant includes a subphthalocyanine derivative represented by Formula (4):

[Chem. 58]

Formula (4)

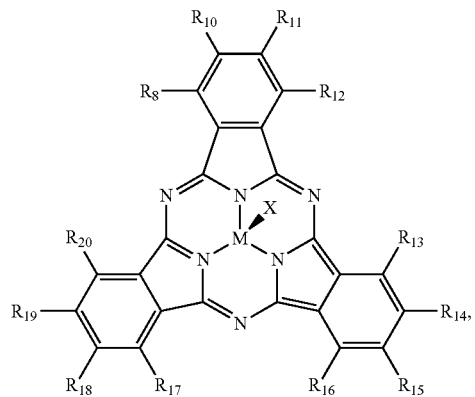

and
$R_9$ to $R_{20}$ in the Formula (4) are each independently selected from a group including hydrogen, halogen, linear, branched or cyclic alkyl, thioalkyl, thioaryl, arylsulfonyl, alkylsulfonyl, amino, alkylamino, arylamino, hydroxy, alkoxy, acylamino, acyloxy, phenyl, carboxy, carboxamido, carboalkoxy, acyl, sulfonyl, cyano and nitro, M represents boron or a divalent or trivalent metal, and X represents an anionic group.

(28) The organic photoelectric conversion element as described above in any one of (20) to (27), in which
the p-type molecules amount to a volume fraction of 10 to 70 percent relative to the photoelectric conversion layer.

REFERENCE SIGNS LIST

200 Solid-state imaging device
210 Row scanning circuit
220 Pixel array section
230 Pixel
231 Transfer transistor
232 Floating diffusion layer
233 Amplifier transistor
234 Selection transistor
240 Organic photoelectric conversion element
241, 311 Upper electrode
242 Charge transport layer
243, 313 Photoelectric conversion layer
244, 315 Lower electrode
245, 316 Substrate
250 DAC
260 Signal processing section
270 Timing control section
280 Column scanning circuit
310 Hole mobility evaluation element
312, 314 Molybdenum oxide layer

The invention claimed is:
1. An organic photoelectric conversion element comprising:
p-type molecules represented by Formula (1) in a photoelectric conversion layer:

Formula (1)

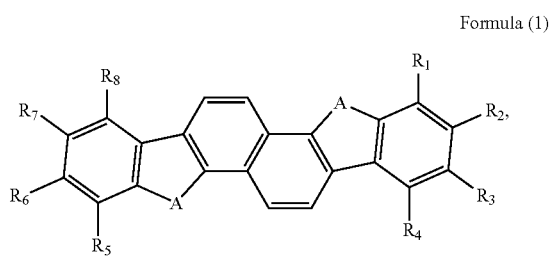

wherein
in the Formula (1), A represents any one of oxygen, sulfur or selenium, any one of $R_1$ to $R_4$ represents a substituted or unsubstituted aryl or heteroaryl having 4 to 30 carbon atoms, the remainder of $R_1$ to $R_4$ each represent hydrogen, any one of $R_5$ to $R_8$ represents a substituted or unsubstituted aryl or heteroaryl having 4 to 30 carbon atoms, and the remainder of $R_5$ to $R_8$ each represent hydrogen,
wherein the photoelectric conversion layer at least includes, as the p-type molecules, a compound represented by Formula (10):

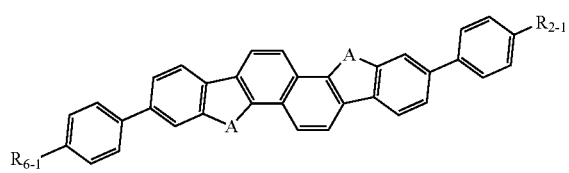

where in the Formula (10), $R_{2-1}$ and $R_{6-1}$ are each a substituted or unsubstituted aryl group or heteroaryl group having 4 to 24 carbon atoms.

2. The organic photoelectric conversion element according to claim 1, wherein
the photoelectric conversion layer further includes n-type molecules, and
the n-type molecules include a fullerene or a fullerene derivative.

3. The organic photoelectric conversion element according to claim 2, wherein
the n-type molecules amount to a volume fraction of 10 to 50 percent relative to the photoelectric conversion layer.

4. The organic photoelectric conversion element according to claim 2, wherein
the n-type molecules include the fullerene derivative represented by any one of Formula (2) or (3):

Formula (2)

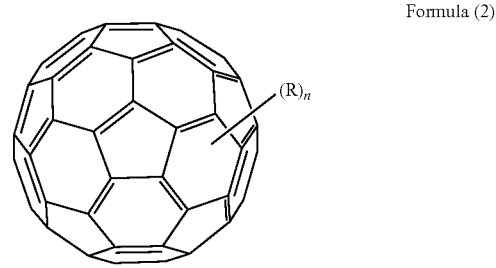

-continued

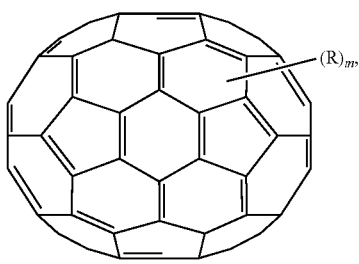

Formula (3)

and in the Formulae (2) and (3), R independently represents hydrogen, halogen, linear, branched or cyclic alkyl, phenyl, a linear or fused-ring aromatic-containing group, a halogenide-containing group, partial fluoroalkyl, perfluoroalkyl, silylalkyl, silylalkoxy, arylsilyl, arylsulfanyl, alkylsulfanyl, arylsulfonyl, alkylsulfonyl, arylsulfido, alkylsulfido, amino, alkylamino, arylamino, hydroxy, alkoxy, acylamino, acyloxy, carbonyl, carboxy, carboxamido, carboalkoxy, acyl, sulfonyl, cyano, nitro, a chalcogenide-containing group, phosphino or phosphono, or a derivative thereof, and n and m each stand for an integer.

5. The organic photoelectric conversion element according to claim 1, wherein
   the photoelectric conversion layer further includes a colorant, and
   the colorant has a maximum absorption coefficient of not smaller than 50000 cm$^{-1}$ in a wavelength range of visible light.

6. The organic photoelectric conversion element according to claim 5, wherein
   the colorant amounts to a volume fraction of 20 to 80 percent relative to the photoelectric conversion layer.

7. The organic photoelectric conversion element according to claim 5, wherein
   the colorant includes a subphthalocyanine derivative.

8. The organic photoelectric conversion element according to claim 7, wherein
   the colorant includes a subphthalocyanine derivative represented by Formula (4):

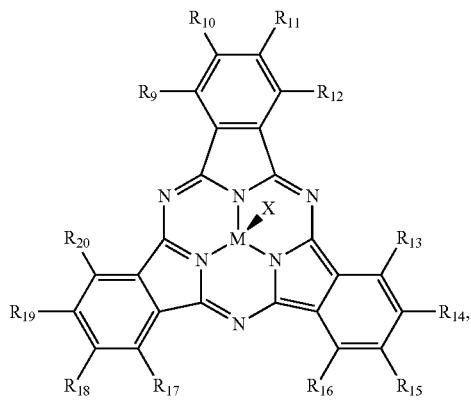

Formula (4)

and $R_9$ to $R_{20}$ in the Formula (4) are each independently selected from a group including hydrogen, halogen, linear, branched or cyclic alkyl, thioalkyl, thioaryl, arylsulfonyl, alkylsulfonyl, amino, alkylamino, arylamino, hydroxy, alkoxy, acylamino, acyloxy, phenyl, carboxy, carboxamido, carboalkoxy, acyl, sulfonyl, cyano and nitro, M represents boron or a divalent or trivalent metal, and X represents an anionic group.

9. The organic photoelectric conversion element according to claim 1, wherein
   the p-type molecules amount to a volume fraction of 10 to 70 percent relative to the photoelectric conversion layer.

10. The organic photoelectric conversion element according to claim 1, wherein
    the photoelectric conversion layer includes, as the p-type molecules, a compound represented by Formula (11) out of the compounds represented by Formula (10):

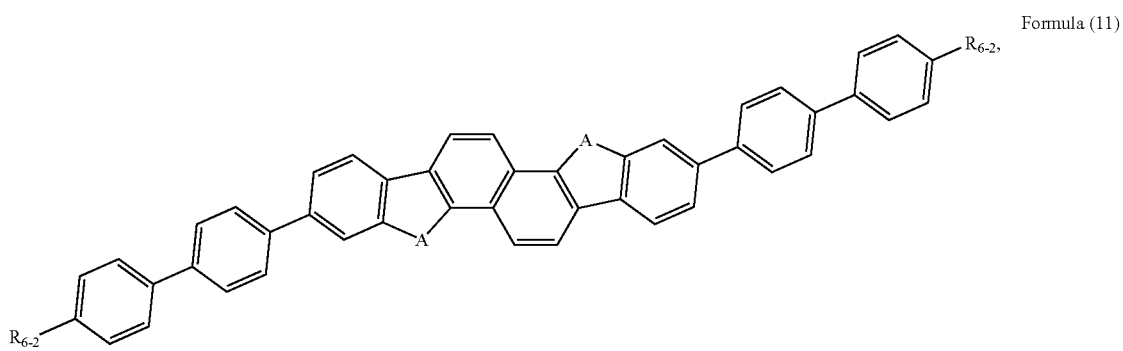

Formula (11)

and in the Formula (11), $R_{2-2}$ and $R_{6-2}$ are each a substituted or unsubstituted aryl group or heteroaryl group having 4 to 18 carbon atoms.

11. The organic photoelectric conversion element according to claim 1, wherein
    the photoelectric conversion layer includes, as the p-type molecules, a compound represented by Formula (12) out of the compounds represented by Formula (10):

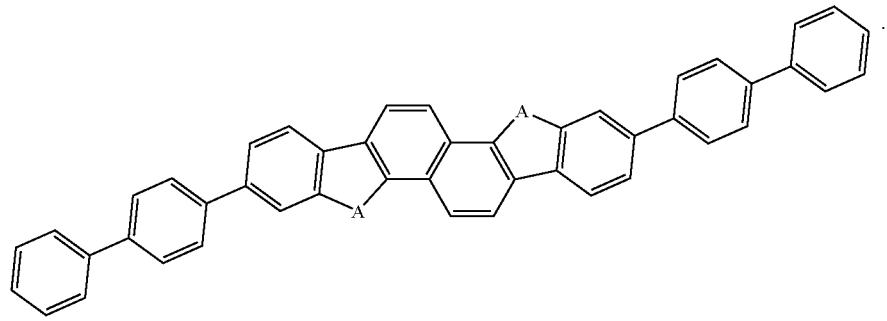

Formula (12)

12. The organic photoelectric conversion element according to claim 11, wherein
the photoelectric conversion layer includes, as the p-type molecules, a compound represented by Formula (13) out of the compounds represented by Formula (12):

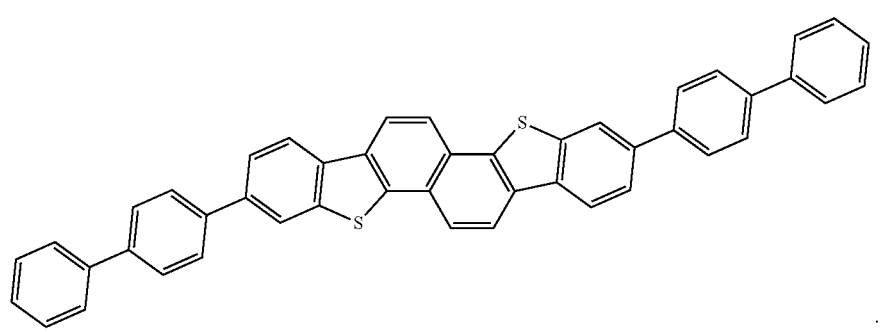

Formula (13)

13. The organic photoelectric conversion element according to claim 1, wherein A is oxygen.

14. The organic photoelectric conversion element according to claim 1, wherein A is sulfur.

15. The organic photoelectric conversion element according to claim 1, wherein A is selenium.

* * * * *